(12) United States Patent
Fang et al.

(10) Patent No.: US 7,642,284 B2
(45) Date of Patent: Jan. 5, 2010

(54) LUMINACIN ANALOGS AND USES THEREOF

(75) Inventors: Frank Fang, Andover, MA (US);
Charles Johannes, Newbury, MA (US);
Ye Yao, North Andover, MA (US);
Xiaojie (Jeff) Zhu, Andover, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/100,194

(22) Filed: Apr. 9, 2008

(65) Prior Publication Data

US 2008/0249320 A1 Oct. 9, 2008

Related U.S. Application Data

(63) Continuation of application No. 10/500,424, filed on May 4, 2005, now abandoned.

(51) Int. Cl.
*A61K 31/351* (2006.01)
*C07D 315/00* (2006.01)

(52) U.S. Cl. ...................... 514/460; 549/416
(58) Field of Classification Search ................ 514/460; 549/416

See application file for complete search history.

(56) References Cited

FOREIGN PATENT DOCUMENTS

| JP | 58116686 | 7/1983 |
|---|---|---|
| JP | 61293920 | 12/1986 |
| JP | 62294619 | 12/1987 |
| JP | 6322583 | 1/1988 |
| JP | 63048213 | 2/1988 |
| JP | 08268888 | 10/1996 |
| WO | WO 99/60000 | 11/1999 |

OTHER PUBLICATIONS

Naruse, et al., "Luminacins: A Family of Capillary Tube Formation Inhibitors from *Streptomyces* sp, I. Taxonomy, Fermentation, Isolation, Physico-chemical Properties and Structure Elucidation", *The Journal of Antibiotics*; 53(6): 579-590, 2000.

Sharma, et al., "USC15A, a non-kinase inhibitor of Src signal transduction", *Oncogene*, 20: 2068-2079, 2001.

Tatsuta, et al., "The first total synthesis and establishment of absolute structure of luminacins $C_1$ and $C_2$", *Tetrahedron Letters*, 42: 7625-7628, 2001.

Wakabayashi, et al., "Luminacins: A Family of Capillary Tube Formation Inhibitors from *Streptomyces* sp., II. Biological Activities", *The Journal of Antibiotics*, 53(6): 591-596, 2000.

International Search Report, PCT/US02/40744, mailed Mar. 28, 2003.

Written Opinion, PCT/US02/40744, mailed Nov. 7, 2003.

International Preliminary Examination Report, PCT/US02/40744, mailed Feb. 19, 2004.

*Primary Examiner*—Taofiq A Solola
(74) *Attorney, Agent, or Firm*—Myers Bigel Sibley & Sajovec, P.A.

(57) ABSTRACT

The present invention provides compounds having formula (I) (and pharmaceutically acceptable derivatives thereof):

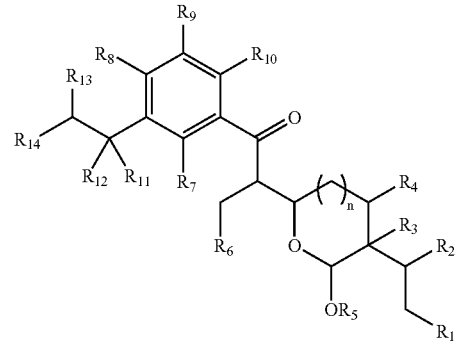

and additionally provides methods for the synthesis thereof and methods for the use thereof in the treatment of cancer, wherein $R_1$-$R_{14}$ and n are as defined herein.

21 Claims, No Drawings

LUMINACIN ANALOGS AND USES THEREOF

PRIORITY CLAIM

The present application is a continuation of and claims priority from U.S. application Ser. No. 10/500,424, filed May 4, 2005 now abandoned which claims priority from PCT International Application No. PCT/US02/40744, filed Dec. 18, 2002, titled LUMINACIN ANALOGS AND USES THEREOF, published in English on Jul. 17, 2003, which claims priority to U.S. Patent Application Ser. No. 60/343,678, filed Dec. 28, 2001, the entire contents of each of which are incorporated herein by reference.

BACKGROUND OF THE INVENTION

Luminacins are novel angiogenesis inhibitors isolated from the fermentation broth of an actinomycete strain designated *Streptomyces* sp. Mer-VD1207. (Naruse et al. *The Journal of Antibiotics*, 2000, Vol. 53, No. 6, 579-590). Fourteen active components were isolated, the structures of which are shown below.

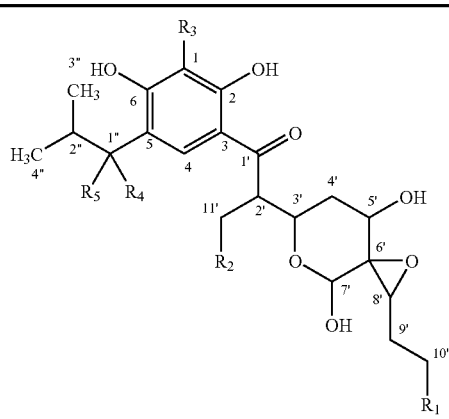

| Luminacin Component | $R_1$ | $R_2$ | $R_3$ | $R_4, R_5$ |
|---|---|---|---|---|
| $A_1$ | H | Et | H | =O |
| $A_2$ | H | Et | H | =O |
| $B_1$ | H | iPr | H | =O |
| $B_2$ | H | iPr | H | =O |
| $C_1$ | H | Et | CHO | OMe, H |
| $C_2$ | H | Et | CHO | OMe, H |
| D | H | Et | CHO | H, H |
| $E_1$ | H | iPr | CHO | OMe, H |
| $E_2$ | H | iPr | CHO | OMe, H |
| $E_3$ | H | Pr | CHO | OMe, H |
| F | $CH_3$ | Et | CHO | H, H |
| $G_1$ | H | iPr | CHO | H, H |
| $G_2$ | H | Pr | CHO | H, H |
| H | H | Et | $COCH_3$ | H, H |

The luminacin components were tested in a rat aorta tube formation (RATF) model, and were shown to inhibit branching and tube formation without decreasing the number of migrating cells (Wakabayashi et al. *The Journal of Antibiotics*, 2000, Vol. 53, No. 6, 591-596). This activity was confirmed in another angiogenesis model using human umbilical vein endothelial cells (HUVEC). The inhibitory activities toward tube formation (RATF model and TF model) and endothelial cell proliferation suggest that these compounds are angiogenesis inhibitors. Molecules closely related or identical to $C_1$ and $C_2$ have also been reported to exhibit activities of immunosuppression (Suzuki et al., *Kokai Tokkyo Koho*, 1983, 116, 686) and low density lipoprotein (LDL) uptake enhancement (Hamaguchi et al., *Kokai Tokkyo Koho*, 1994, 228, 144). The relationship, if any, of these activities to the angiogenic activity remains to be established.

The newly developing field of angiogenesis inhibitors has vast applications in the treatment of many incurable diseases like cancer. Thus these types of compounds have the potential to significantly impact modern medicine. Accordingly, the demonstrated ability of luminacins to inhibit angiogenesis has generated an interest in further exploring the biological and pharmacological activity of luminacins and analogues thereof. Clearly, there remains a need to develop practical synthetic methodologies to access and examine the therapeutic effect of a variety of novel luminacin analogues, particularly those that are inaccessible by making modifications to the natural product. It would also be of particular interest to develop novel compounds that exhibit a favorable therapeutic profile in vivo (e.g., are safe and effective, while retaining stability in biological media).

SUMMARY OF THE INVENTION

As discussed above, there remains a need for the development of novel therapeutic agents and agents useful for treating disorders that involve angiogenic activity. The present invention provides novel compounds of general formula (I),

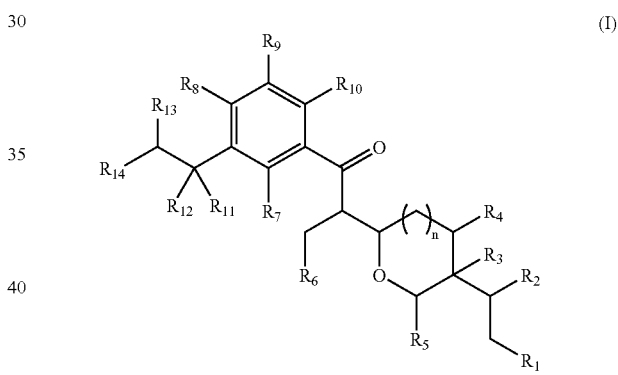

and pharmaceutical compositions thereof, as described generally and in subclasses herein, which compounds are useful as angiogenesis inhibitors, and thus are useful, for example, for the treatment of angiogenesis-related disorders, including, for example, cancer or proliferative disorders.

DESCRIPTION OF CERTAIN PREFERRED EMBODIMENTS OF THE INVENTION

In recognition of the need to develop novel and effective cancer therapies, the present invention provides novel synthetic methodologies enabling access to luminacin analogs having a broad range of biological and pharmacological activity. In one aspect, the present invention provides novel luminacin compounds, as described in more detail herein, which demonstrate potent anti-angiogenesis activity. Thus, the compounds of the invention, and pharmaceutical compositions thereof, are useful as angiogenesis inhibitors for the treatment of cancer.

1) General Description of Compounds of the Invention

The compounds of the invention include compounds of the general formula (I) as further defined below:

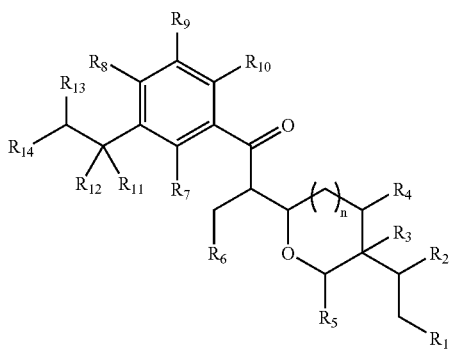

and pharmaceutically acceptable derivatives thereof,
wherein n is 0, 1 or 2;

$R_1$ is hydrogen or an aliphatic, heteroaliphatic, aryl or heteroaryl moiety;

$R_2$ and $R_3$ are each independently hydrogen, or, when taken together, may be —O— or —$(CH_2)_q$—, where q is 1, 2 or 3;

$R_4$ is hydrogen, hydroxyl, protected hydroxyl or $OR^i$, or an aliphatic or heteroaliphatic moiety,
wherein $R^i$ is an aliphatic or heteroaliphatic moiety;

$R_5$ is hydrogen, hydroxyl, protected hydroxyl or $OR^{ii}$, or an aliphatic or heteroaliphatic moiety,
wherein $R^{ii}$ is an aliphatic or heteroaliphatic moiety, or wherein $R_1$ and $R_5$, when taken together, may form a cycloaliphatic or heterocycloaliphatic moiety comprising 6 to 12 atoms;

$R_6$ is hydrogen, or an aliphatic, heteroaliphatic, aryl or heteroaryl moiety;

$R_7$ is hydrogen, hydroxyl, protected hydroxyl, $OR^{iii}$, or an aliphatic or heteroaliphatic moiety,
wherein $R^{iii}$ is an aliphatic or heteroaliphatic moiety;

$R_8$ is hydrogen, hydroxyl, protected hydroxyl or $OR^{iv}$,
wherein $R^{iv}$ is an aliphatic or heteroaliphatic moiety;

$R_9$ is hydrogen, —$CF_3$, —CHO, imine, hydrazone, oxime, carboxylic acid, carboxylic ester, acyl halide, ketone, amide, acetal, anhydride, dihalide, epoxide, nitrile or an aliphatic or heteroaliphatic moiety;

$R_{10}$ is hydroxyl or protected hydroxyl;

$R_{11}$ and $R_{12}$ are each independently hydrogen, hydroxyl or $OR^v$, or an aliphatic or heteroaliphatic moiety, or, when taken together, may be —(C=O)—;
wherein $R^v$ is an aliphatic or heteroaliphatic moiety;

and $R_{13}$ and $R_{14}$ are each independently hydrogen, or an aliphatic, heteroaliphatic, aryl or heteroaryl moiety;

whereby each of the foregoing aliphatic and heteroaliphatic moieties may independently be substituted or unsubstituted, cyclic or acyclic, linear or branched, and whereby each of the foregoing aryl and heteroaryl moieties may be substituted or unsubstituted.

In certain embodiments of compounds described directly above and compounds as described in certain classes and subclasses herein, the following groups do not occur simultaneously as defined:

$R_4$, $R_5$, $R_8$ and $R_{10}$ are hydroxyl, $R_{13}$ and $R_{14}$ are methyl, $R_2$ and $R_3$ are taken together to form an epoxide, n is 1 and:

(i) $R_1$ is methyl, $R_9$ is hydrogen, $(R_{11}, R_{12})$ is (=O) and $R_6$ is ethyl or isopropyl;

(ii) $R_1$ is methyl drogen, $R_9$ is CHO, $(R_{11}, R_{12})$ is (OMe, H) and $R_6$ is ethyl, propyl or isopropyl;

(iii) $R_1$ is methyl, $R_9$ is CHO, $R_{11}$ and $R_{12}$ are hydrogen and $R_6$ is ethyl, propyl or isopropyl;

(iv) $R_1$ is methyl, $R_9$ is $COCH_3$, $R_{11}$ and $R_{12}$ are hydrogen and $R_6$ is ethyl; and (v) $R_1$ is ethyl, $R_9$ is CHO, $R_{11}$ and $R_{12}$ are hydrogen and $R_6$ is ethyl.

In certain embodiments, the present invention defines certain classes of compounds which are of special interest. For example, one class of compounds of special interest includes those compounds in which n is 1 and the compound has the structure:

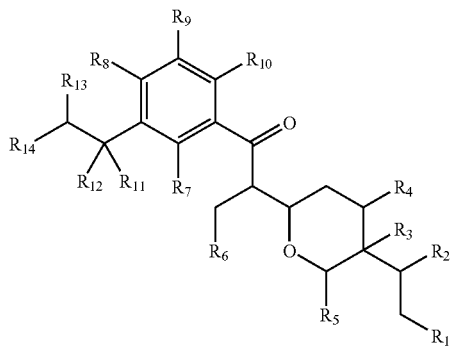

wherein $R_1$-$R_{14}$ are as previously defined.

Another class of compounds of special interest consists of compounds in which $R_{10}$ is OH and the compound has the structure:

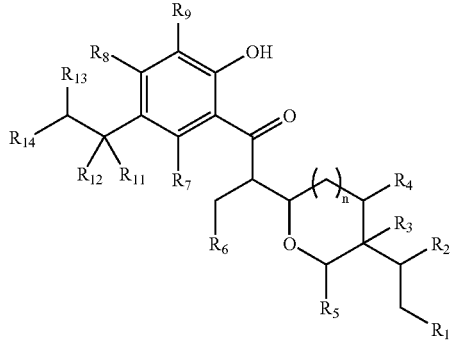

wherein $R_1$-$R_9$, $R_{11}$-$R_{14}$ and n are as previously defined.

Another class of compounds of special interest consists of compounds in which $R_{14}$ is aryl and the compound has the structure:

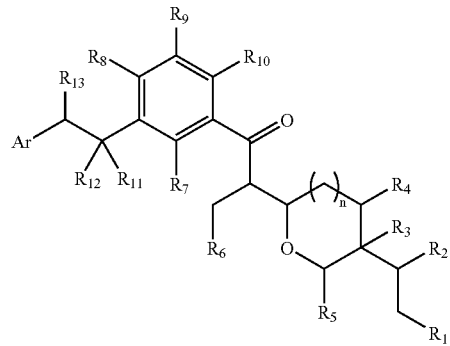

wherein $R_1$-$R_{13}$ and n are as previously defined.

Another class of compounds of special interest consists of compounds in which $R_2$, and $R_3$, taken together, form an epoxide and the compound has the structure:

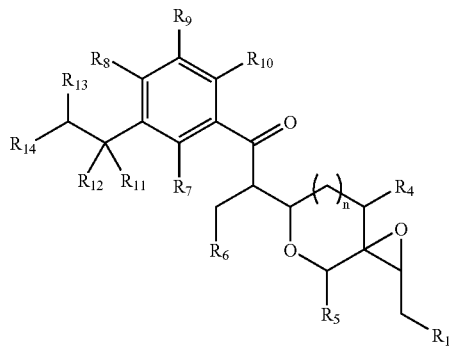

wherein $R_1$, $R_4$-$R_{14}$ and n are as previously defined.

Another class of compounds of special interest consists of compounds in which $R_4$ is hydroxyl and the compound has the structure:

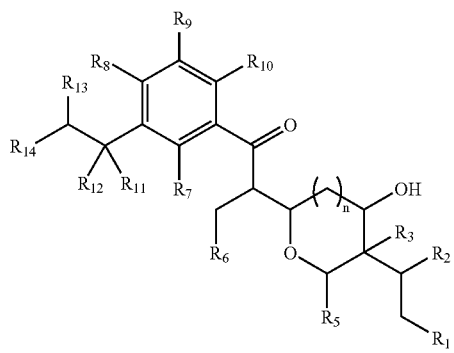

wherein $R_1$-$R_3$, $R_5$-$R_{14}$ and n are as previously defined.

A number of important subclasses of each of the foregoing classes deserve separate mention; these subclasses include subclasses of the foregoing classes in which:

i) $R_1$ is hydrogen or lower alkyl, wherein the alkyl substitutent may be substituted or unsubstituted, linear or branched or cyclic or acyclic;

ii) $R_2$ and $R_3$ are independently hydrogen or, when taken together, form a cyclopropyl moiety or an epoxide;

iii) $R_4$ is hydroxyl;

iv) $R_5$ is hydroxyl or lower alkoxyl, wherein the alkoxyl substitutent may be substituted or unsubstituted, linear or branched or cyclic or acyclic;

v) $R_6$ is lower alkyl, wherein the alkyl substitutent may be substituted or unsubstituted, linear or branched or cyclic or acyclic;

vi) $R_7$ is hydrogen, hydroxyl, lower alkyl or lower alkoxyl, wherein the alkyl and alkoxyl substitutents may be substituted or unsubstituted, linear or branched or cyclic or acyclic;

vii) $R_8$ is hydrogen, hydroxyl or protected hydroxyl;

viii) $R_9$ is —CHO or —CH$_2$OR$^{vi}$, wherein R$^{vi}$ is hydrogen, protecting group or an aliphatic moiety, wherein the aliphatic moiety may be substituted or unsubstituted, linear or branched or cyclic or acyclic;

ix) $R_{10}$ is hydroxyl;

x) $R_{11}$ and $R_{12}$ are independently hydrogen or lower alkoxyl, wherein the alkoxyl substitutent may be substituted or unsubstituted, branched or unbranched or cyclic or acyclic;

xi) $R_{13}$ and $R_{14}$ are independently hydrogen, lower alkyl or aryl, wherein the alkyl substitutent may be substituted or unsubstituted, branched or unbranched or cyclic or acyclic, and wherein the aryl substitutent may be substituted or unsubstituted; and/or xi) $R_5$ is hydroxyl or lower alkoxyl, $R_6$ is lower alkyl, $R_7$ is hydrogen, hydroxyl, lower alkyl or lower alkoxyl, $R_8$ is hydrogen, hydroxyl or protected hydroxyl, $R_9$ is —CHO or —CH$_2$OR$^{vi}$, $R_{11}$ and $R_{12}$ are independently hydrogen or lower alkoxyl, and $R_{13}$ is lower alkyl; wherein R$^{vi}$ is hydrogen, protecting group or an aliphatic or heteroaliphatic moiety; whereby each of the foregoing alkyl, alkoxyl, aliphatic and heteroaliphatic moieties may be independently substituted or unsubstituted, linear or branched, or cyclic or acyclic.

The following structures illustrate several exemplary types of compounds of these classes. Additional compounds are described in the Exemplification herein. Other compounds of the invention will be readily apparent to the reader:

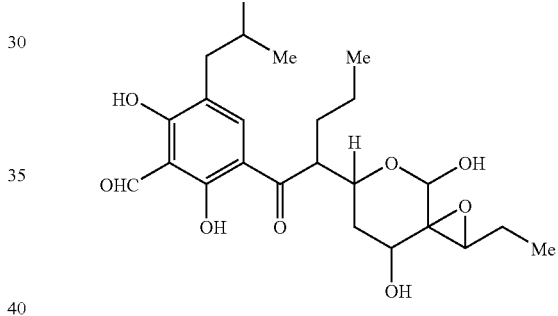

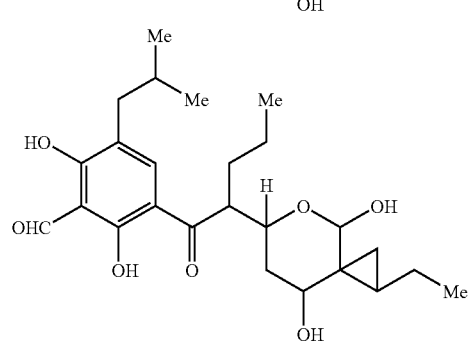

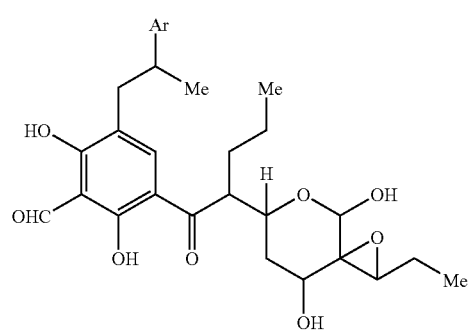

-continued

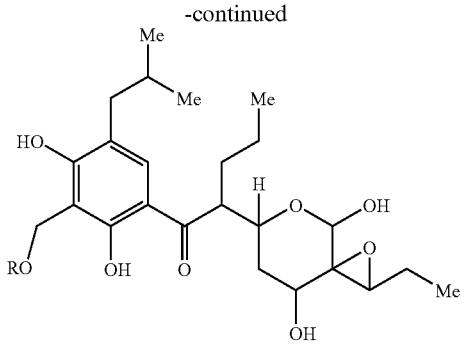

As the reader will appreciate, compounds of particular interest include, among others, those which share the attributes of one or more of the foregoing subclasses. Some of those subclasses are illustrated by the following sorts of compounds:

I) Compounds of the Formula (and Pharmaceutically Acceptable Derivatives Thereof):

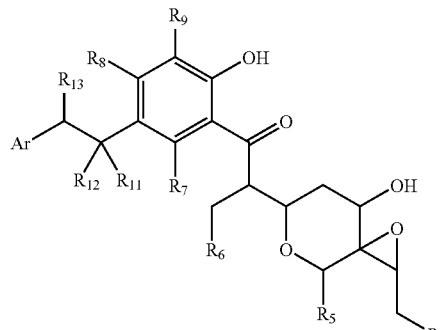

(I)

wherein n is 0, 1 or 2;

$R_1$ is hydrogen or lower alkyl;

$R_2$ and $R_3$ are independently hydrogen or, when taken together, form a cyclopropyl moiety or an epoxide;

$R_4$ is hydrogen, hydroxyl or protected hydroxyl;

$R_5$ is hydroxyl or lower alkoxyl;

$R_6$ is lower alkyl;

$R_7$ is hydrogen, hydroxyl, lower alkyl or lower alkoxyl;

$R_8$ is hydrogen, hydroxyl or protected hydroxyl;

$R_9$ is —CHO or —CH$_2$OR$^{vi}$, wherein R$^{vi}$ is hydrogen, protecting group or an aliphatic moiety;

$R_{10}$ is hydroxyl or protected hydroxyl;

$R_{11}$ and $R_{12}$ are independently hydrogen or lower alkoxyl; and $R_{13}$ and $R_{14}$ are independently hydrogen, lower alkyl or aryl;

whereby each of the foregoing alkyl, alkoxyl and aliphatic moieties may independently be substituted or unsubstituted, cyclic or acyclic, linear or branched, and whereby each of the foregoing aryl moieties may be substituted or unsubstituted.

II) Compounds of the Formula (and Pharmaceutically Acceptable Derivatives Thereof):

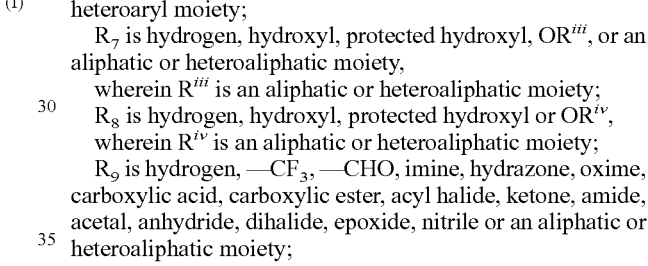

wherein $R_1$ is hydrogen or an aliphatic, heteroaliphatic, aryl or heteroaryl moiety;

$R_5$ is hydrogen, hydroxyl, protected hydroxyl or OR$^{ii}$, or an aliphatic or heteroaliphatic moiety,
wherein R$^{ii}$ is an aliphatic or heteroaliphatic moiety, or
wherein $R_1$ and $R_5$, when taken together, may form a cycloaliphatic or heterocycloaliphatic moiety comprising 6 to 12 atoms;

$R_6$ is hydrogen, or an aliphatic, heteroaliphatic, aryl or heteroaryl moiety;

$R_7$ is hydrogen, hydroxyl, protected hydroxyl, OR$^{iii}$, or an aliphatic or heteroaliphatic moiety,
wherein R$^{iii}$ is an aliphatic or heteroaliphatic moiety;

$R_8$ is hydrogen, hydroxyl, protected hydroxyl or OR$^{iv}$,
wherein R$^{iv}$ is an aliphatic or heteroaliphatic moiety;

$R_9$ is hydrogen, —CF$_3$, —CHO, imine, hydrazone, oxime, carboxylic acid, carboxylic ester, acyl halide, ketone, amide, acetal, anhydride, dihalide, epoxide, nitrile or an aliphatic or heteroaliphatic moiety;

$R_{11}$ and $R_{12}$ are each independently hydrogen, hydroxyl or OR$^{v}$, or an aliphatic or heteroaliphatic moiety, or, when taken together, may be —(C=O)—;
wherein R$^{v}$ is an aliphatic or heteroaliphatic moiety;

$R_{13}$ is independently hydrogen, or an aliphatic, heteroaliphatic, aryl or heteroaryl moiety; and Ar is aryl;

whereby each of the foregoing aliphatic and heteroaliphatic moieties may independently be substituted or unsubstituted, cyclic or acyclic, linear or branched, and whereby each of the foregoing aryl and heteroaryl moieties may be substituted or unsubstituted.

III) Compounds of the Formula (and Pharmaceutically Acceptable Derivatives Thereof):

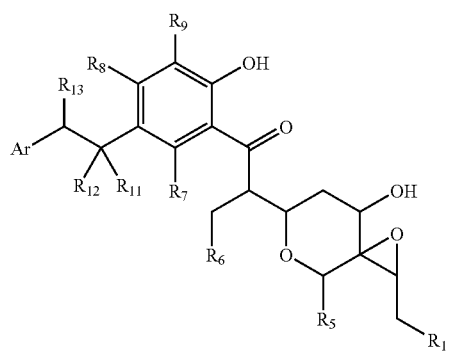

wherein $R_1$ is hydrogen or lower alkyl;

$R_5$ is hydroxyl or lower alkoxyl;
$R_6$ is lower alkyl;
$R_7$ is hydrogen, hydroxyl, lower alkyl or lower alkoxyl;
$R_8$ is hydrogen, hydroxyl or protected hydroxyl;
$R_9$ is —CHO or —CH$_2$OR$^{vi}$;
wherein R$^{vi}$ is hydrogen, protecting group or an aliphatic or heteroaliphatic moiety;
$R_{11}$ and $R_{12}$ are independently hydrogen or lower alkoxyl;
$R_{13}$ is lower alkyl; and
Ar is aryl;
whereby each of the foregoing alkyl, alkoxyl, aliphatic and heteroaliphatic moieties may be independently substituted or unsubstituted, linear or branched, or cyclic or acyclic.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (J) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

2) Compounds and Definitions

As discussed above, this invention provides novel compounds with a range of biological properties. Compounds of this invention have biological activities relevant for the treatment of diseases or other disorders such as proliferative diseases, including, but not limited to cancer. More generally, the compounds are useful in the regulation of angiogenesis.

Compounds of this invention include those specifically set forth above and described herein, and are illustrated in part by the various classes, subgenera and species disclosed elsewhere herein.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vitro to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999; the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl-n, hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl group employed in the invention contains 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "dialkylamino" refers to a group having the structure —$N(R^1)_2$ where $R^1$ is alkyl, as defined herein. The term "aminoalkyl" refers to a group having the structure $NH_2R'$—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl group employed in the invention contains 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —CHOH; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. It will also be appreciated that aryl and heteroaryl moieties, as defined herein may be attached via an aliphatic, heteroaliphatic, alkyl or heteroalkyl moiety and thus also include -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)heteroaryl moieties. Thus, as used herein, the phrases "aryl or heteroaryl" and "aryl, heteroaryl, -(aliphatic)aryl, -(heteroaliphatic)aryl, -(aliphatic)heteroaryl, -(heteroaliphatic) heteroaryl, -(alkyl)aryl, -(heteroalkyl)aryl, -(heteroalkyl) aryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or heterocyclic moieties, may optionally be substituted with substituents including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CHOH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties which contain one or more oxygen sulfur, nitrogen, phosphorus or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$, independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The terms "halo", "halogen" and "halide" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one or more of the hydrogen atoms thereon with but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$, independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substitutents described above and herein may be substituted or unsubstituted. Additional examples or generally applicable substituents are illustrated by the specific embodiments shown in the Examples which are described herein.

The term "carboxylic acid" as used herein refers to a group of formula —COOH.

The term "carboxylic ester" as used herein refers to a group of formula —CO$_2$R$_x$, wherein R$_x$ includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted.

The term "imine" as used herein refers to a group of formula —CR$_y$=NR$_x$, wherein R$_x$ and R$_y$ are independently hydrogen or an aliphatic, heteroaliphatic, aryl, heteroaryl, alkylaryl, or alkylheteroaryl moiety, wherein any of the aliphatic, heteroaliphatic, alkylaryl, or alkylheteroaryl moieties described above and herein may be substituted or unsubstituted, branched or unbranched, cyclic or acyclic, and wherein any of the aryl or heteroaryl moieties described above and herein may be substituted or unsubstituted.

The term "hydrazone" as used herein refers to a group of formula —CR$_y$=NHR$_x$, wherein R$_x$, and R$_Y$ are independently hydrogen or an aliphatic, heteroaliphatic, aryl, heteroaryl, alkylaryl, or alkylheteroaryl moiety, wherein any of the aliphatic, heteroaliphatic, alkylaryl, or alkylheteroaryl moieties described above and herein may be substituted or unsubstituted, branched or unbranched, cyclic or acyclic, and wherein any of the aryl or heteroaryl moieties described above and herein may be substituted or unsubstituted.

The term "oxime" as used herein refers to a group of formula —CR$_x$=NOH, wherein R$_x$ includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted.

The term "acyl halide" as used herein refers to a group of formula —(C=O)X, wherein X is a halide as defined above.

The term "amide" as used herein refers to a group of formula —(C=O)NR$_x$R$_y$, wherein R$_x$ and R$_Y$ are independently hydrogen or an aliphatic, heteroaliphatic, aryl, heteroaryl, alkylaryl, or alkylheteroaryl moiety, wherein any of the aliphatic, heteroaliphatic, alkylaryl, or alkylheteroaryl moieties described above and herein may be substituted or unsubstituted, branched or unbranched, cyclic or acyclic, and wherein any of the aryl or heteroaryl moieties described above and herein may be substituted or unsubstituted.

The term "acetal" as used herein refers to a group of formula —CR$_z$(OR$_x$)(OR$_y$) wherein R$_z$ includes, but is not limited to, hydrogen or an aliphatic, heteroaliphatic, aryl, heteroaryl, alkylaryl, or alkylheteroaryl moiety, R$_x$ and R$_y$ are independently an aliphatic, heteroaliphatic, aryl, heteroaryl, alkylaryl, or alkylheteroaryl moiety, wherein R$_x$ and R$_y$, when taken together, may form a heterocycloaliphatic moiety comprising 5-7 atoms; and wherein any of the aliphatic, heteroaliphatic, alkylaryl, or alkylheteroaryl moieties described above and herein may be substituted or unsubstituted, branched or unbranched, cyclic or acyclic, and wherein any of the aryl, heteroaryl or heterocycloaliphatic moieties described above and herein may be substituted or unsubstituted.

The term "anhydride" as used herein refers to a group of formula —C(=O)OC(=O)R$_x$, wherein R$_x$ is an aliphatic, heteroaliphatic, aryl, heteroaryl, alkylaryl, or alkylheteroaryl moiety, wherein any of the aliphatic, heteroaliphatic, alkylaryl, or alkylheteroaryl moieties described above and herein may be substituted or unsubstituted, branched or unbranched, cyclic or acyclic, and wherein any of the aryl or heteroaryl moieties described above and herein may be substituted or unsubstituted.

3) Synthetic Methodology

In recognition of the need for an efficient and practical route to luminacin analogues, the present invention provides novel synthetic methodologies for the synthesis of this class of therapeutic agents. Although the synthesis of luminacin D (also referred to herein as VD1207D) is described specifically herein directly below (and in the Examples), it will be appreciated that this methodology is generally applicable to the generation of analogues and derivatives.

In one aspect, the present invention provides novel luminacin analogs having formula (I) a described above and in certain classes and subclasses herein. An overview of the synthesis of the inventive compounds is provided below, as detailed in Schemes 1-9, and in the Exemplification herein. It will be appreciated that the methods as described herein can be applied to each of the compounds as disclosed herein and equivalents thereof. Additionally, the reagents and starting materials are well known to those skilled in the art. Although the following schemes describe certain exemplary compounds, it will be appreciated that the use of alternate starting materials will yield other analogs of the invention. For example, compounds are described below where R$_2$ and R$_3$ are taken together to form an epoxide; however, it will be appreciated that alternate starting materials and/or intermediates can be utilized to generate compounds where R$_2$ and R$_3$ are hydrogen or are taken together to form a cyclopropyl ring, etc.

In certain embodiments, compounds as provided herein, are prepared from a general advance intermediate, as depicted below (20):

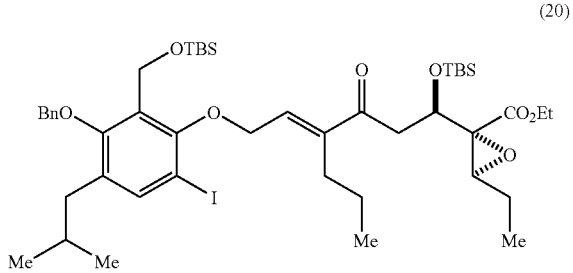

(20)

In certain embodiments, synthetic manipulations of general advance intermediate 20 include two intramolecular cyclizations, as depicted in Scheme 1. Intermediate 20 leads to the formation of four diastereomers at C2' and C3', which can be separated by HPLC and/or flash chromatography. Each diastereomer leads in turn to the preparation of a luminacin analog through a series of synthetic steps (see for example the synthesis of VD1207D depicted in Scheme 2).

Scheme 1
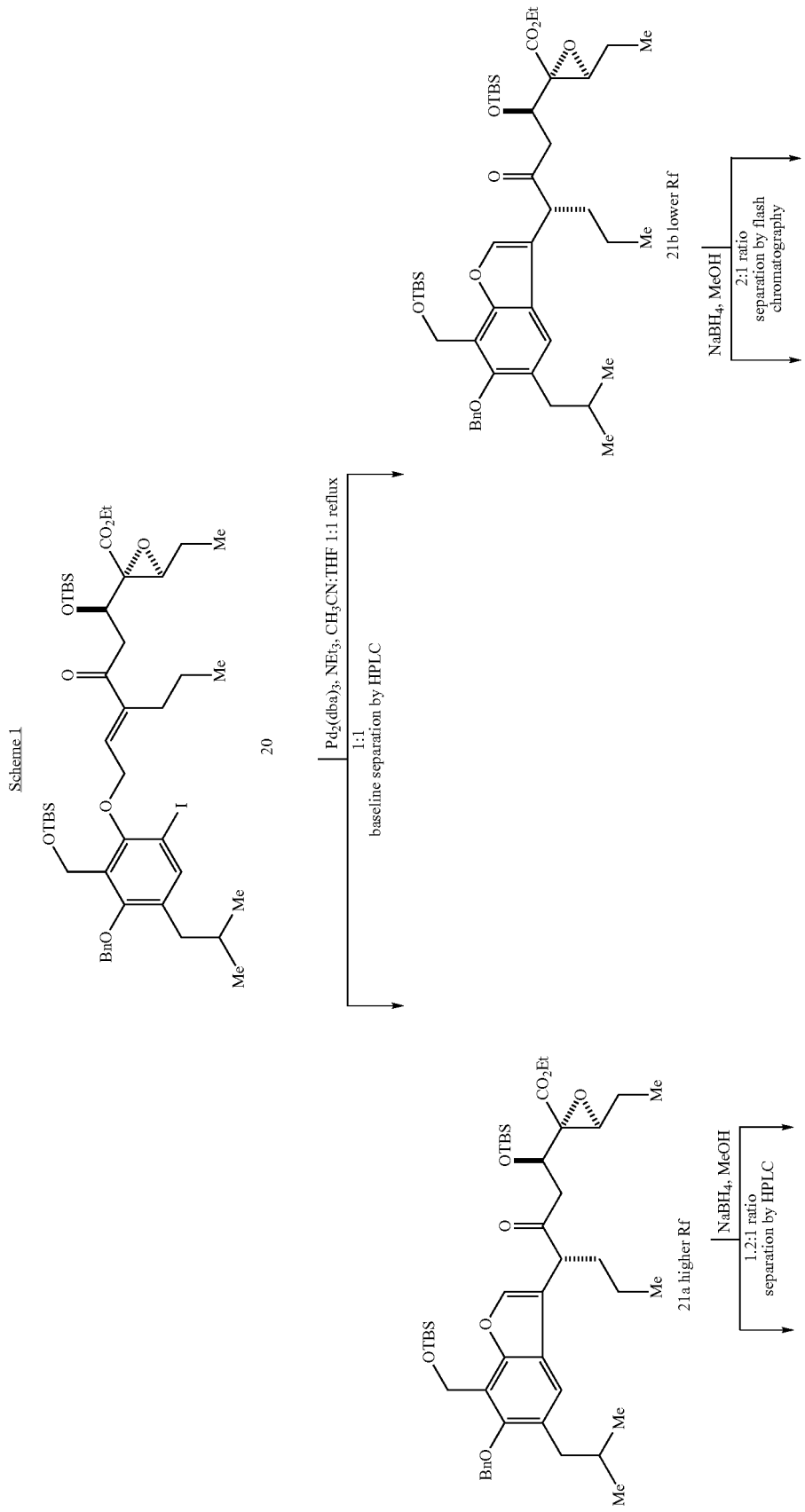

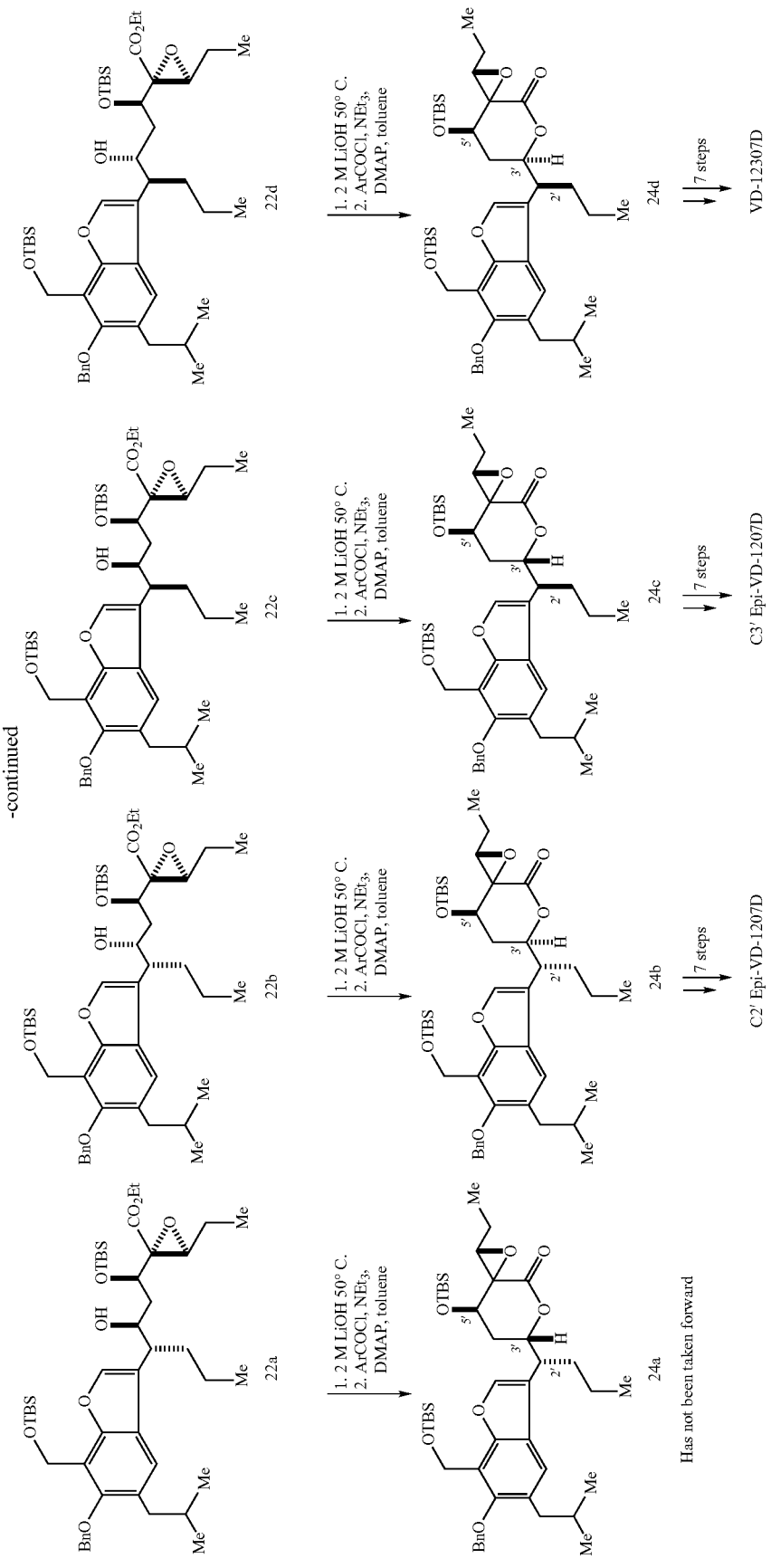

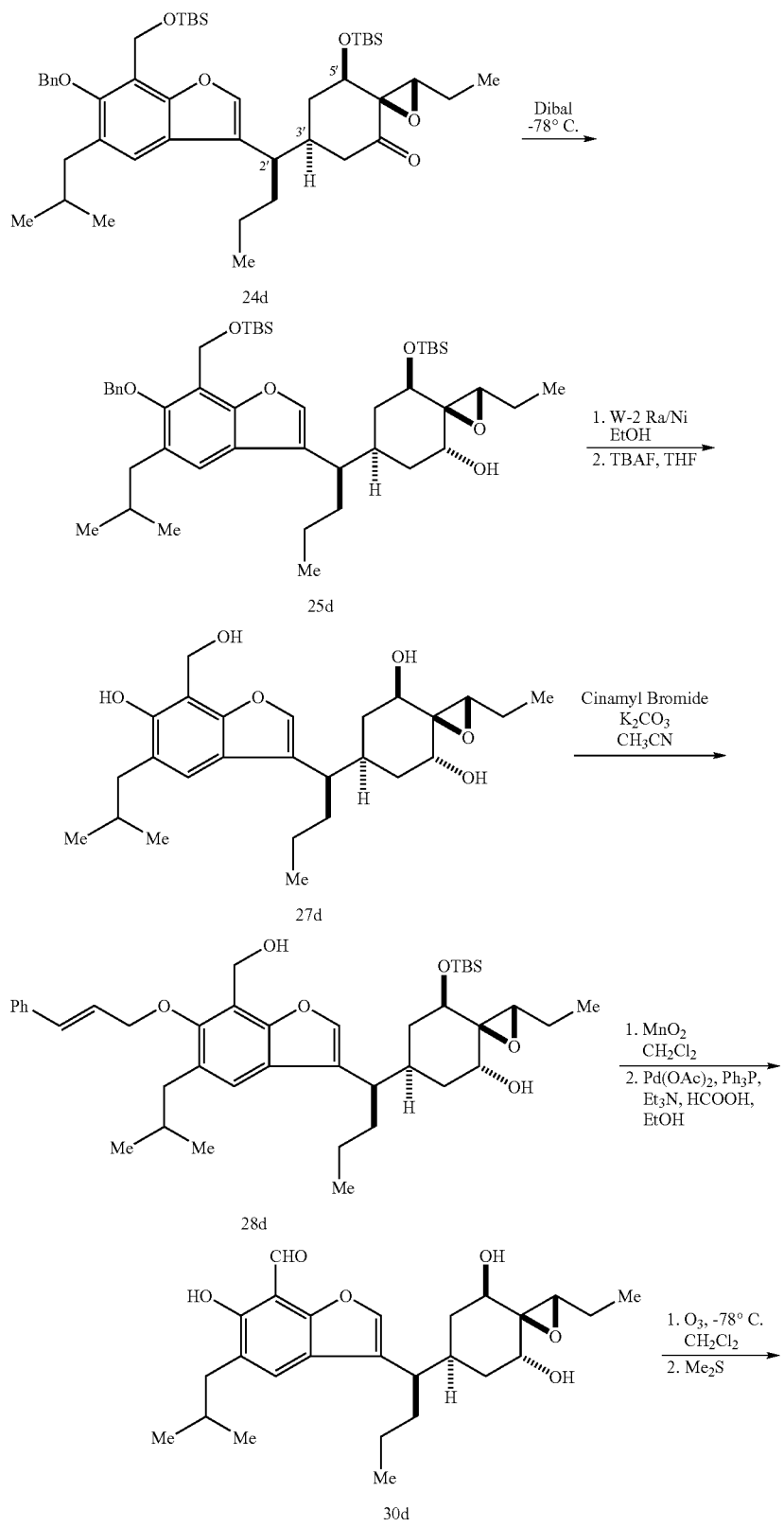
Scheme 2

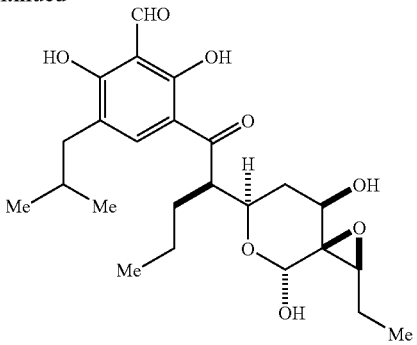

VD-1207D

In certain embodiments, general advance intermediate 20 can be synthesized from two components: an aromatic component, the synthesis of which is depicted in Scheme 3 and is described in more detail in examples herein, and an aldehyde component, the synthesis of which is depicted in Scheme 4 and is described in more detail in examples herein. As depicted in Scheme 5, and as described in more detail in examples herein, these two components are coupled, and subsequent oxidation to generate the general advance intermediate (20) occurs.

Scheme 3

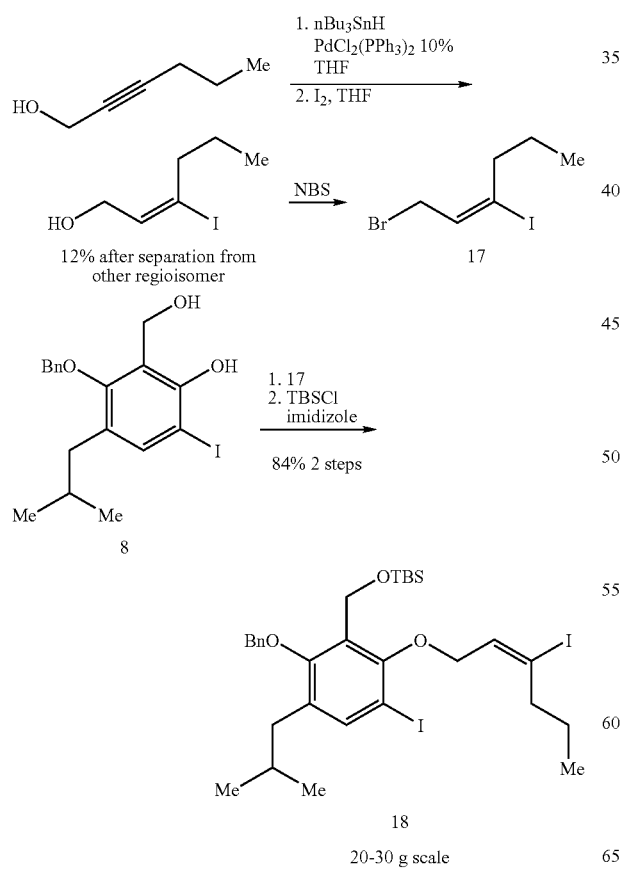

Scheme 4

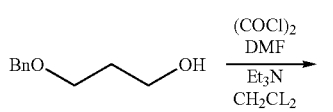

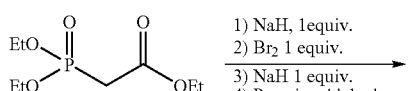

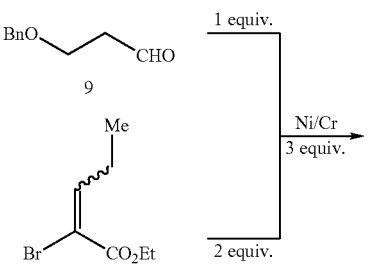

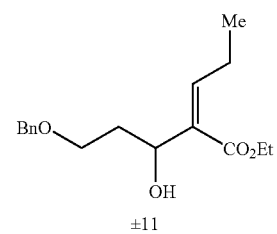

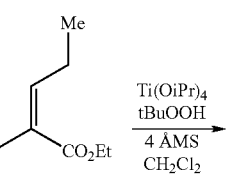

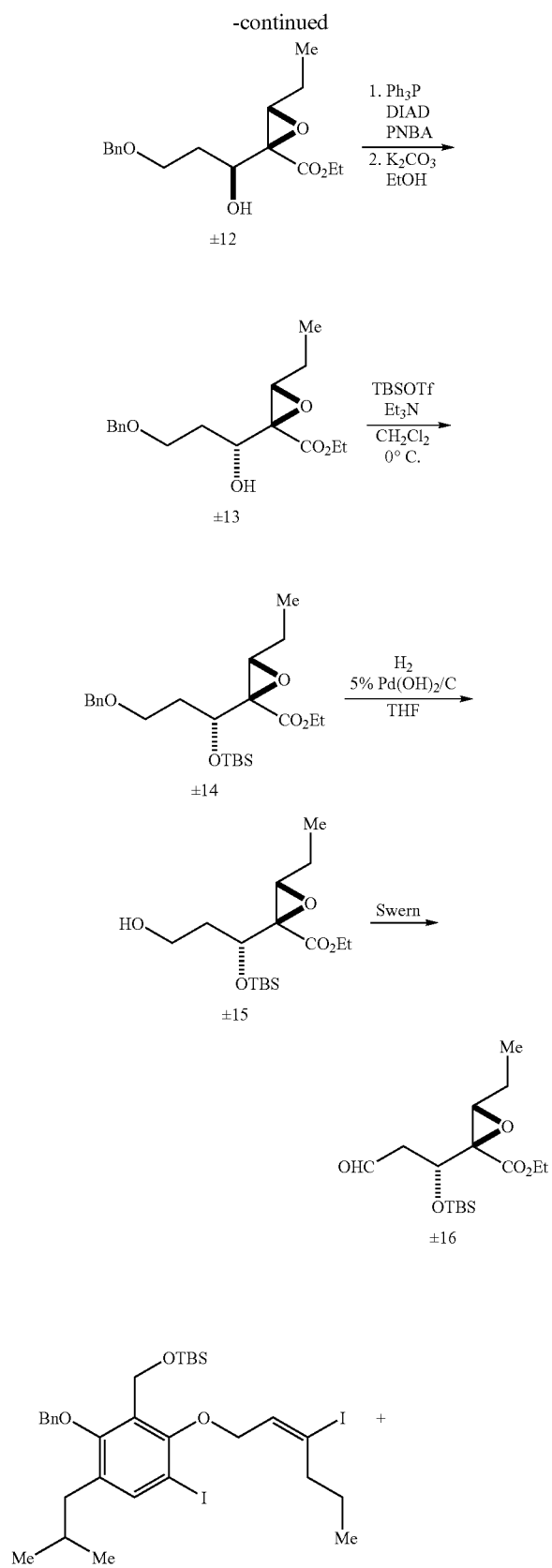
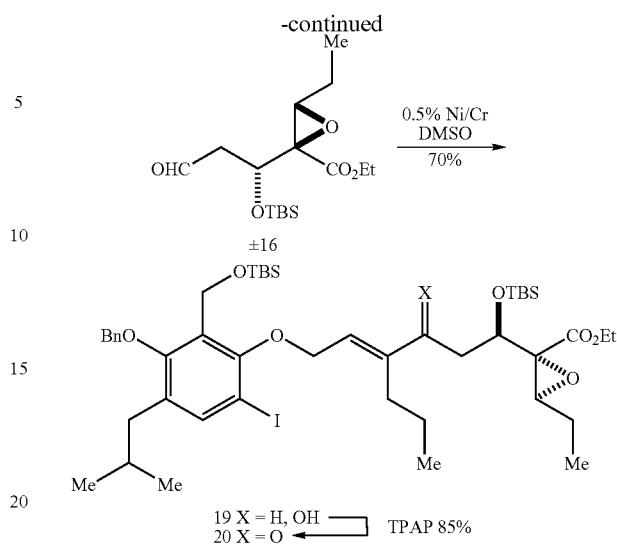

It will be appreciated that each of the steps as described above can be carried out using reagents and conditions as described for the synthesis of VD1207D, or they may be modified using other available reagents. For example, a variety of lactonisation conditions, aromatic nucleus functionalization and asymmetric epoxidation and/or hydroxylation conditions are well-known in the art and can be utilized in the method of the invention. See, generally, March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers; the entire contents of which are incorporated herein by reference.

As mentioned above, it will also be appreciated that each of the components used in the synthesis of analogues can be diversified either before synthesis or alternatively after the construction of the luminacin construct. As used herein, the term "diversifying" or "diversify" means reacting an inventive compound, as defined herein, at one or more reactive sites to modify a functional moiety or to add a functional moiety. For example, the aromatic ring can be diversified (prior to or after reaction) to either add functionality (e.g., where hydrogen is present, a halogen or other functionality can be added) or to modify functionality (e.g., where a hydroxyl group is present on the aromatic ring, the aromatic ring can be diversified by reacting with a reagent to protect the hydroxyl group, or to convert it into an aliphatic or heteroaliphatic moiety). Described generally below are a variety of schemes to assist the reader in the synthesis of a variety of analogues, either by diversification of the intermediate components or by diversification of the luminacin construct.

In certain embodiments, components used in the synthesis of the core structure of the compounds of the invention are diversified to give structurally related luminacin derivatives. In certain embodiments, the invention encompasses compounds obtained by varying the structure of the aromatic nucleus (A) or the tetrahydropyran component (B) of the inventive compounds of formula (I), as illustrated below:

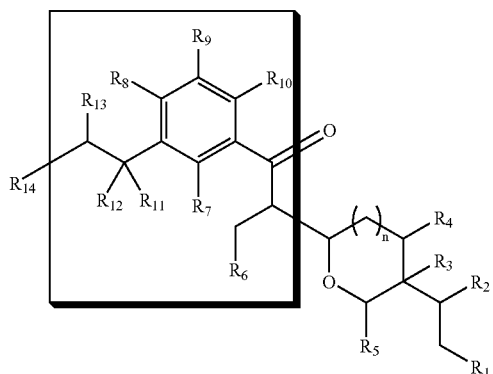

(A)

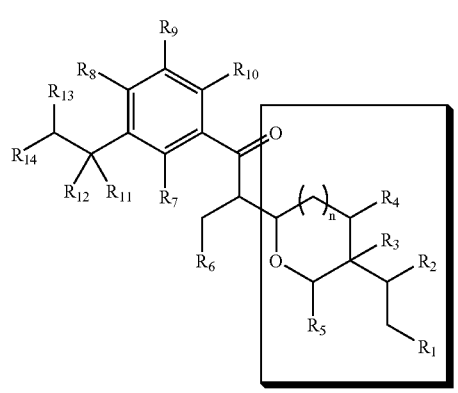

(B)

In certain embodiments, the preparation of chemically diverse derivatives may be achieved by diversifying a benzofuran intermediate, such as that obtained by the synthetic method detailed in Scheme 6. Examples of chemical transformations suitable to achieve such derivatization include, but are not limited to, hetero-Diels Alder, Aldol condensation, reductive amination, metathesis, alkylation and Wittig-Horner-Emmons, as depicted in Scheme 7. In addition, as described above, the aromatic ring can be diversified (prior to or after reaction) to either add functionality (e.g., where hydrogen is present, a halogen or other functionality can be added) or to modify functionality (e.g., where a hydroxyl group is present on the aromatic ring, the aromatic ring can be diversified by reacting with a reagent to protect the hydroxyl group, or to convert it into an aliphatic or heteroaliphatic moiety). Subsequent oxidative cleavage of the benzofuran nucleus, such as that depicted in Scheme 2 (last synthetic step), would generate a library of structurally related luminacin derivatives comprising an aryl moiety.

Scheme 6

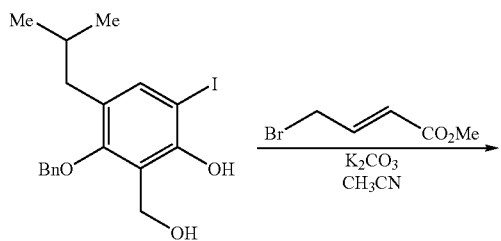

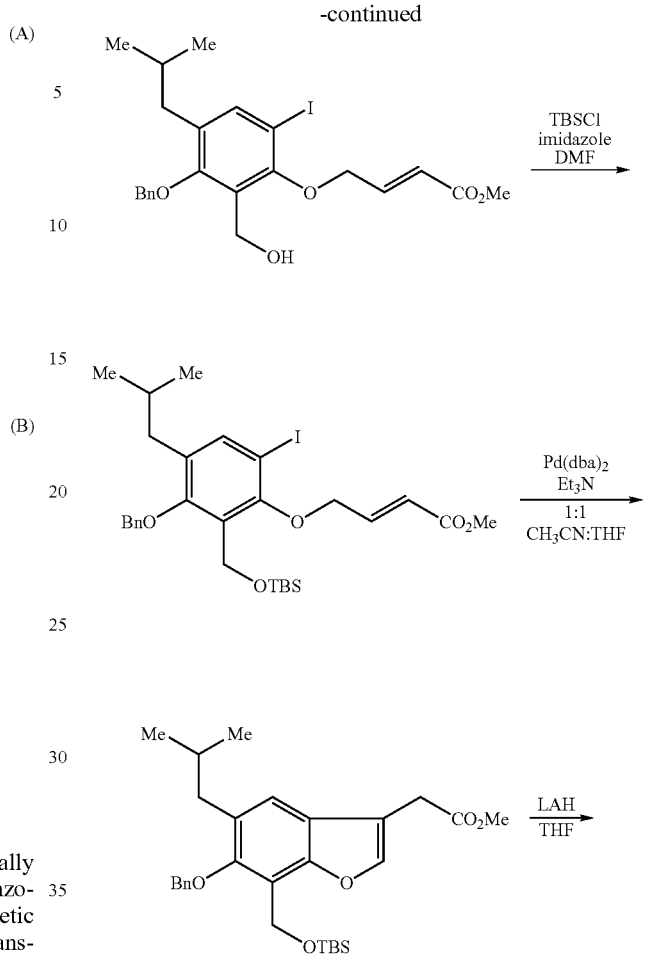

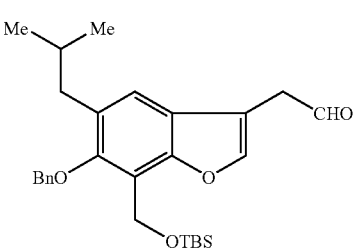

Scheme 7
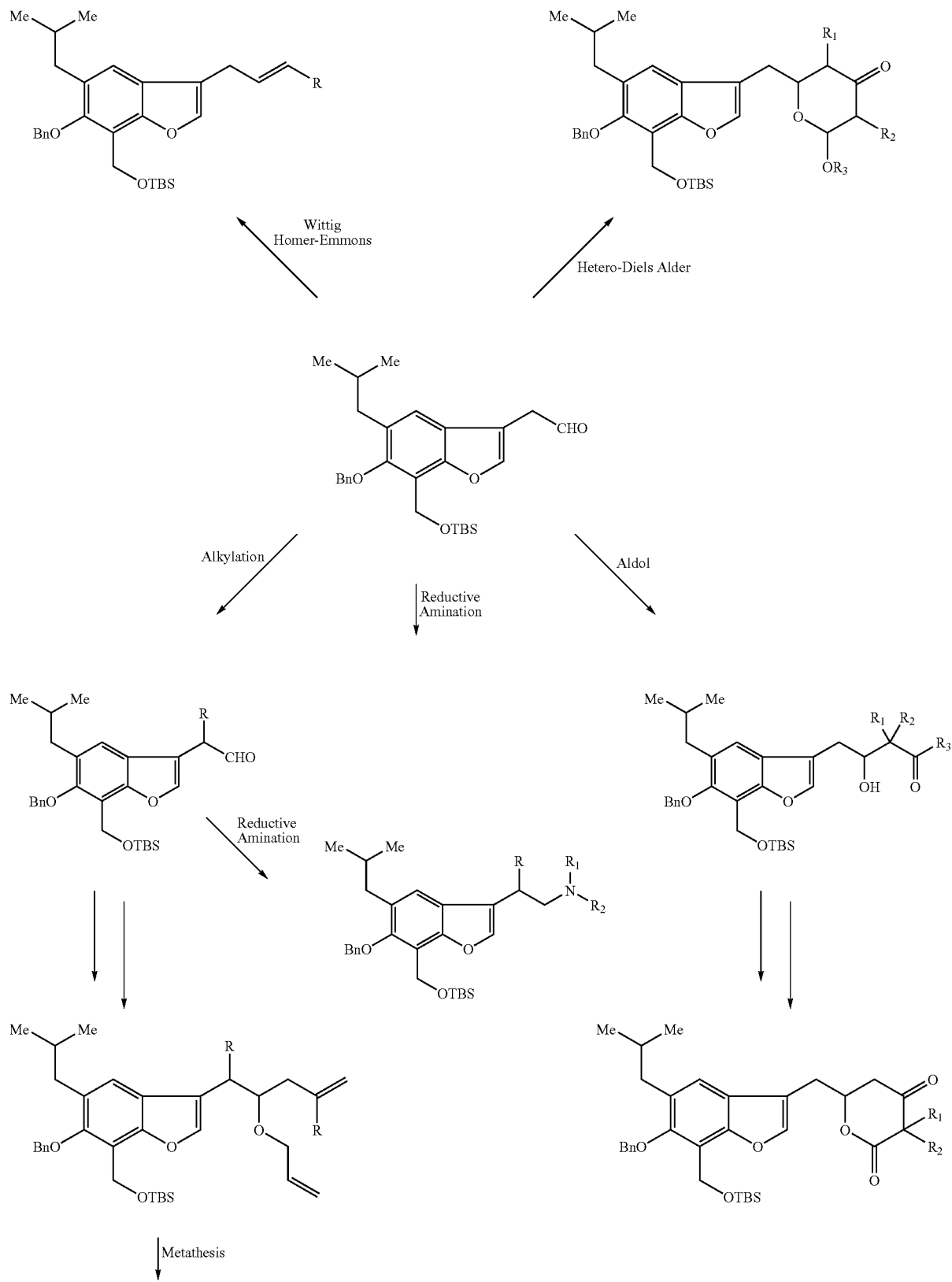

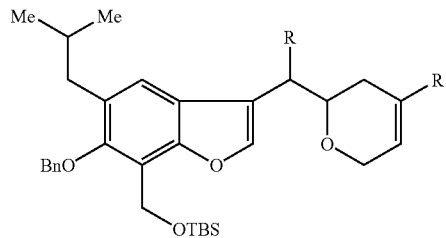

In other embodiments, the preparation of chemically diverse derivatives may be achieved by diversifying the tetrahydropyran component of the compounds of the invention, as depicted in Scheme 8. One skilled in the art will recognize that possible chemical transformations suitable to achieve diversification of the tetrahydropyran moiety are not limited to those depicted in Scheme 8. Rather, any suitable synthetic methods known in the art can be used to achieve desired chemical transformations.

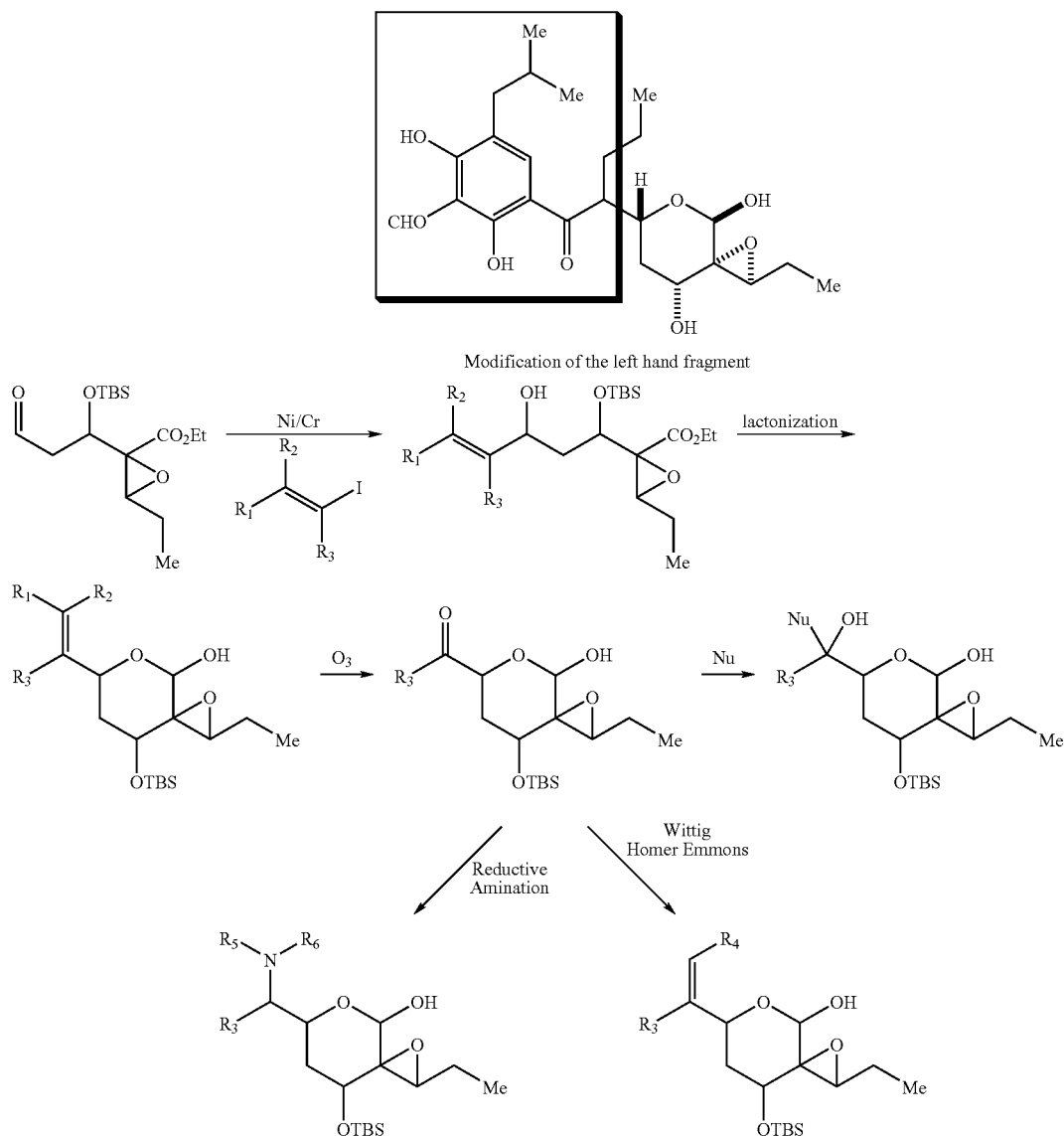

As detailed above, a variety of reactions can be utilized to diversify the luminacin core structures after assembly of the luminacin construct. Scheme 9 illustrates a few examples of such reactions. A person of ordinary skill in the art will appreciate that suitable chemical diversification methods are not limited to those depicted in Scheme 9, and that any suitable synthetic methods known in the art can be used to achieve desired chemical transformations.

4) Research Uses, Formulation and Administration

According to the present invention, the inventive compounds may be assayed in any of the available assays known in the art for identifying compounds having a pre-determined biological activity. For example, the assay may be cellular or non-cellular, in vivo or in vitro, high- or low-throughput format, etc. In certain exemplary embodiments, the inventive

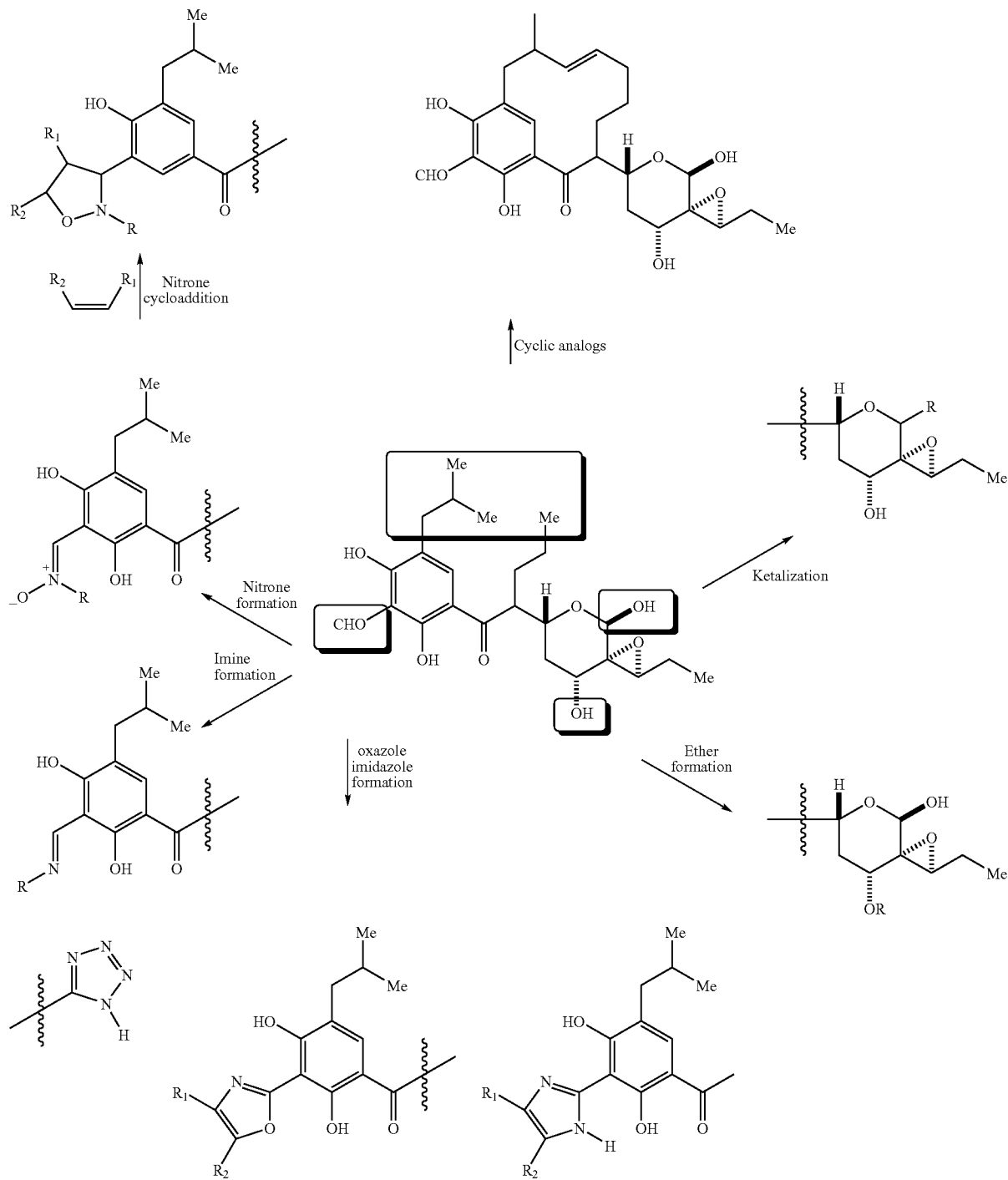

Scheme 9 compounds are tested in assays to identify those compounds having angiogenesis inhibitory activity and/or antiproliferative/anticancer activity.

Thus, in one aspect, compounds of this invention which are of particular interest include those which:
- exhibit cytotoxic or growth inhibitory effect on cancer cell lines maintained in vitro or in animal studies using a scientifically acceptable cancer cell xenograft model;
- exhibit an antiangiogenic effect on solid tumors;
- exhibit a favorable therapeutic profile (e.g., safety, efficacy, and stability).

As detailed in the exemplification herein, in assays to determine the ability of compounds to inhibit proliferation of certain cell-lines, certain inventive compounds exhibited IC50 values less than 7 µM. In other embodiments, exemplary compounds exhibited IC50 values less than 1 µM. In still other embodiments, the cytotoxicity of certain compounds was evaluated in vitro. Certain of these compounds exhibited IC50 values less than 15 µM. In other embodiments, exemplary compounds exhibited IC50 values less than 30 µM.

This invention also provides a pharmaceutical preparation comprising at least one of the compounds as described above and herein, or a pharmaceutically acceptable derivative thereof, which compounds are capable of inhibiting the growth of or killing cancer cells. The invention further provides a method for inhibiting tumor growth and/or tumor metastasis.

As discussed above, certain of the compounds as described herein act as inhibitors of tumor angiogenesis and thus are useful in the treatment of cancer and in the inhibition of tumor growth and in the killing of cancer cells. The invention further provides a method for inhibiting tumor growth and/or tumor metastasis. The method involves the administration of a therapeutically effective amount of the compound or a pharmaceutically acceptable derivative thereof to a subject (including, but not limited to a human or animal) in need of it. In certain embodiments, the inventive compounds are useful for the treatment of solid tumors. In still other embodiments of interest, the inventive compounds are useful for the treatment of glioblastoma, retinoblastoma, breast cancer, cervical cancer, colon and rectal cancer, leukemia, lung cancer (including, but not limited to small cell lung cancer), melanoma, multiple myeloma, non-Hodgkin's lymphoma, ovarian cancer, pancreatic cancer, prostate cancer and gastric cancer.

Pharmaceutical Compositions

As discussed above this invention provides novel compounds that have biological properties useful for the treatment of cancer. Accordingly, in another aspect of the present invention, pharmaceutical compositions, are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be a cytotoxic agent or anticancer agent approved for the treatment of cancer, as discussed in more detail herein, or it may be any one of a number of agents undergoing approval in the Food and Drug Administration that ultimately obtain approval for the treatment of an immune disorder or cancer. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may induce metal salts such as alkali metal salts, e.g., sodium or potassium salts, and alkaline earth metal salts, e.g., calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulifonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses and Formulations of Compounds of the Invention

As described in more detail herein, in general, the present invention provides compounds useful for the treatment of cancer. Specifically, certain compounds of the invention have been shown to inhibit the proliferation of human umbilical vein endothelial cells (HUVEC) in vitro, as described in more detail herein, and are useful for the treatment of cancer, including solid tumors.

As discussed above, compounds of the invention exhibit anti-angiogenesis activity. As such, compounds of the invention are particularly useful for the treatment of diseases and disorders associated with increased angiogenesis, including, but not limited to, cancer.

Angiogenesis, the proliferation and migration of endothelial cells resulting in the formation of new blood vessels, is a physiological component of reproductive functions, normal growth, and development, as well as wound healing. Angiogenesis is also observed in a variety of diseases such as diabetic retinopathy, arthritis, and inflammation. In addition, angiogenesis has been demonstrated to play important roles in the progression of cancer by allowing tumor growth and facilitating formation of metastases. The development of blood vessels within tumor tissues is closely correlated with invasion and metastasis of cancer cells in breast cancer, melanoma, lung cancer, prostate cancer and other cancers. Consequently, inhibition of angiogenesis may lead to control of tumor growth and metastasis. In addition, the use of angiogenesis inhibitors presents certain advantages over standard chemotherapy treatment in that angiogenesis inhibitors target dividing endothelial cells rather than tumor cells. Thus, Anti-angiogenic drugs are not likely to cause bone marrow suppression, gastrointestinal symptoms, or hair loss; symptoms characteristic of standard chemotherapy treatments. Furthermore, drug resistance is a major problem with existing standard chemotherapy agents. This stems from the fact that most cancer cells are genetically unstable, are more prone to mutations and are therefore likely to produce drug resistant cells. Since angiogenic drugs target normal endothelial cells, which are not genetically unstable, drug resistance is less likely to develop.

Thus, as described above, in one aspect of the invention, methods for the treatment of cancer are provided comprising administering a therapeutically effective amount of a compound of formula (I), as described generally in classes and subclasses herein, to a subject in need thereof. In certain embodiments of the present invention a "therapeutically effective amount" of the inventive compound or pharmaceutical composition is that amount effective for detectable killing or inhibiting the growth of cancer cells. Thus, the expression "effective amount" as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As discussed above, in one aspect, the compounds of the present invention are useful as anticancer agents, and thus may be useful in the treatment of cancer, by effecting tumor cell death or inhibiting the growth of tumor cells. In general, the inventive anticancer agents are useful in the treatment of cancers and other proliferative disorders, including, but not limited to glioblastoma, retinoblastomas, breast cancer, cervical cancer, colon and rectal cancer, leukemia, lung cancer (including, but not limited to small cell lung cancer), melanoma, multiple myeloma, non-Hodgkin's lymphoma, ovarian cancer, pancreatic cancer, prostate cancer, and gastric cancer, to name a few.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In certain embodiments, the pharmaceutical compositions of the present invention further comprise one or more additional therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Exemplification

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

Certain exemplary compounds of the invention are listed below and are referred to by compound number as indicated.

| Ref. number | Compound |
|---|---|
| 805583 | 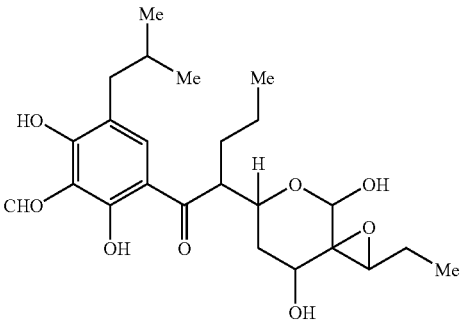<br>Racemic |
| 805615 | 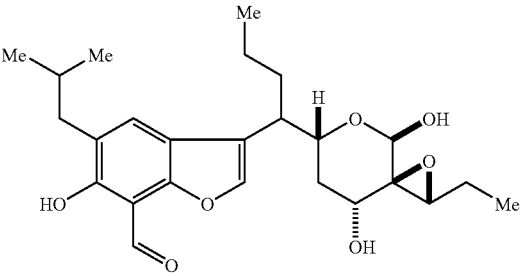<br>Racemic<br>C2' Bottom, C3' Bottom |
| 805632 | 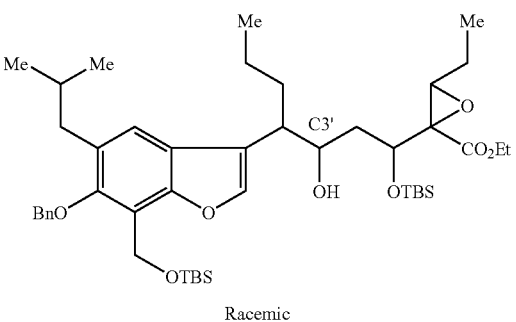<br>Racemic |

-continued
| Ref. number | Compound |
|---|---|
| 805633 | 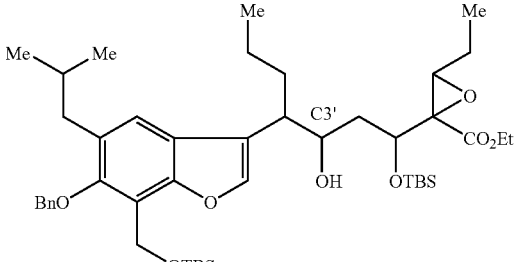<br>C3' Epimer (Racemic) |
| 805641 | 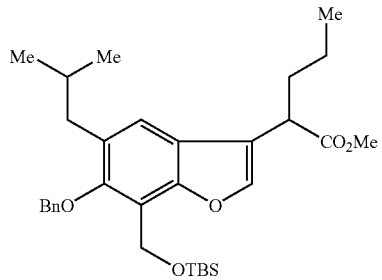 |
| 805640 | 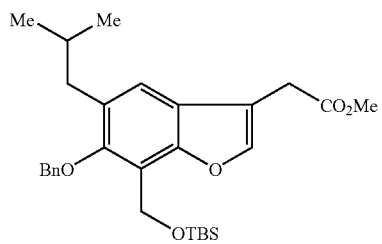 |
| 805727 | 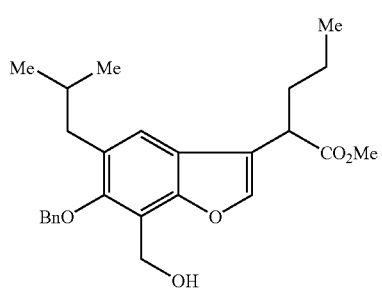 |
| 805728 | 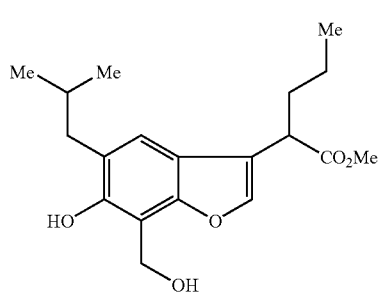 |

-continued
| Ref. number | Compound |
|---|---|
| 805729 | 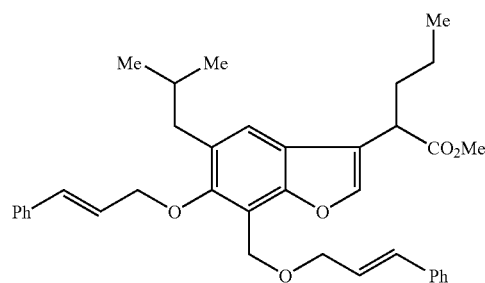 |
| 805730 | 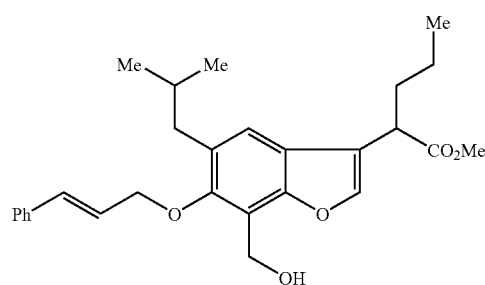 |
| 805731 | 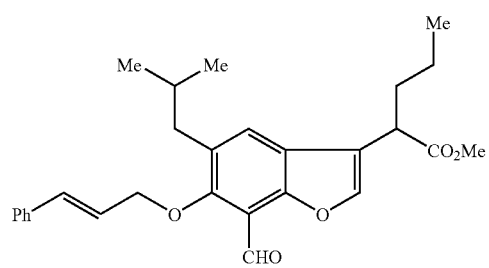 |
| 805732 | 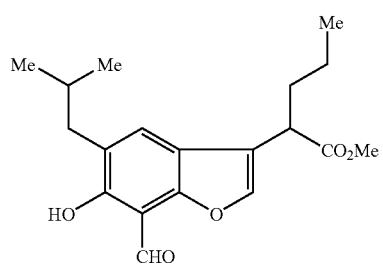 |
| 805733 | 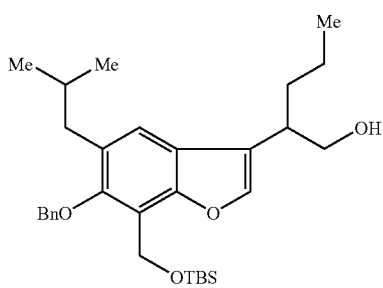 |

| Ref. number | Compound |
| --- | --- |
| 805754 | 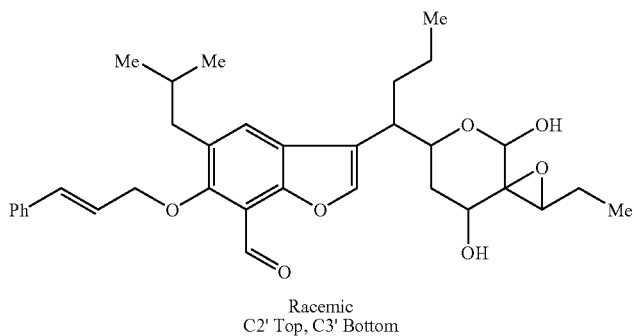<br>Racemic<br>C2' Top, C3' Bottom |
| 805755 | 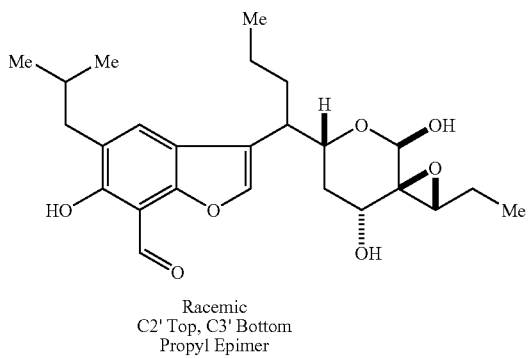<br>Racemic<br>C2' Top, C3' Bottom<br>Propyl Epimer |
| 805757 | 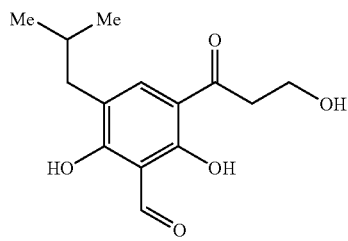 |
| 805758 | 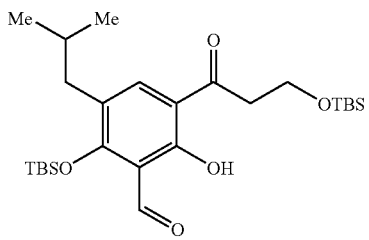 |
| 805759 | 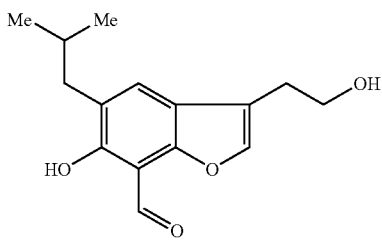 |

| Ref. number | Compound |
|---|---|
| 805760 | (structure: 3,5-disubstituted-2,4-dihydroxybenzaldehyde with isobutyl group and 3-(OTBS)propanoyl group) |
| 805828 | (structure: ethyl 2-(1-hydroxy-3-(benzyloxy)propyl)pent-2-enoate with Me group) |
| 805829 | (structure: ethyl 3-ethyl-2-(1-hydroxy-3-(benzyloxy)propyl)oxirane-2-carboxylate) |
| 805866 | (structure: benzaldehyde derivative with isobutyl, dihydroxy, and 2-(methoxycarbonyl)pentanoyl groups) |
| 805867 | (structure: benzofuran with isobutyl, OBn, CH₂OTBS, and 2-hydroxyethyl substituents) |
| 805868 | (structure: benzofuran with isobutyl, OBn, CH₂OH, and 2-hydroxyethyl substituents) |

-continued

| Ref. number | Compound |
|---|---|
| 805869 | 5-isobutyl-6-(benzyloxy)-3-(2-hydroxyethyl)benzofuran-7-carbaldehyde |
| 805870 | 5-isobutyl-6-(benzyloxy)-3-(2-((tert-butyldimethylsilyl)oxy)ethyl)benzofuran-7-carbaldehyde |
| 805873 | 3-(benzyloxy)-5-(3-((tert-butyldimethylsilyl)oxy)propanoyl)-6-hydroxy-4-isobutylbenzaldehyde |
| 805888 | (5-isobutyl-6-(benzyloxy)-3-(1-hydroxypentan-2-yl)benzofuran-7-yl)methanol |
| 805890 | (5-isobutyl-6-(benzyloxy)-3-(1-(benzyloxy)pentan-2-yl)benzofuran-7-yl)methanol |
| 805892 | 3-(benzyloxy)-5-(3-(benzyloxy)propanoyl)-6-hydroxy-4-isobutylbenzaldehyde |

| Ref. number | Compound |
|---|---|
| 805893 | 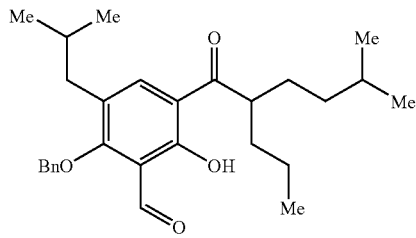 |
| 805907 | 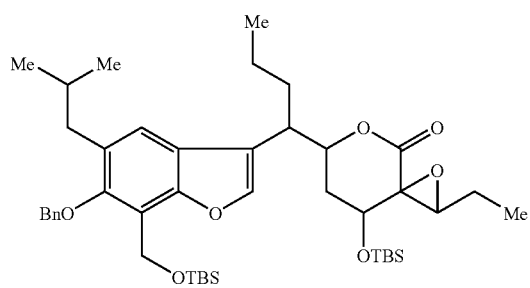
Racemic
C2' bottom, C3' bottom |
| 805908 | 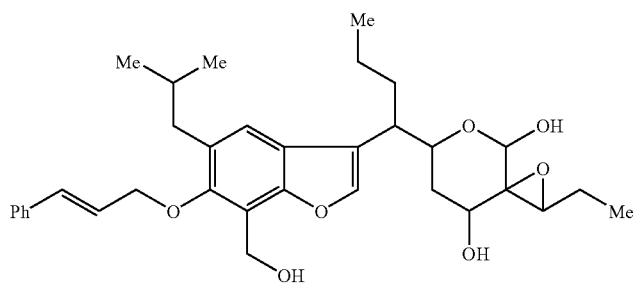
Racemic
C2' bottom, C3' bottom |
| 805909 | 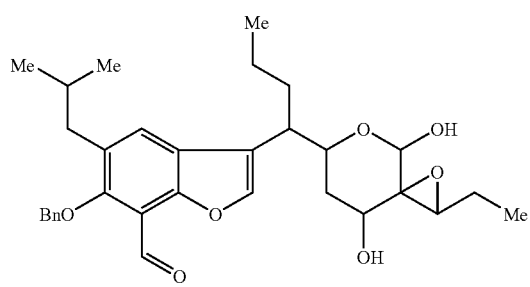
Racemic
C2' bottom, C3' bottom |

| Ref. number | Compound |
|---|---|
| 805910 | 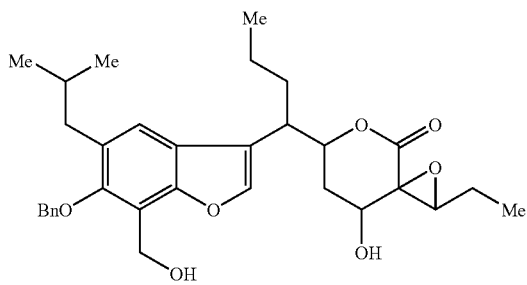<br>Racemic<br>C2' bottom, C3' bottom |
| 805926 | 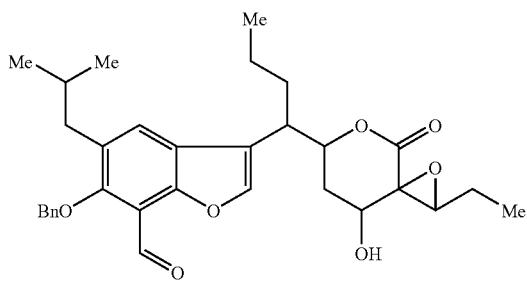<br>Racemic<br>C2' bottom, C3' bottom |
| 805955 | 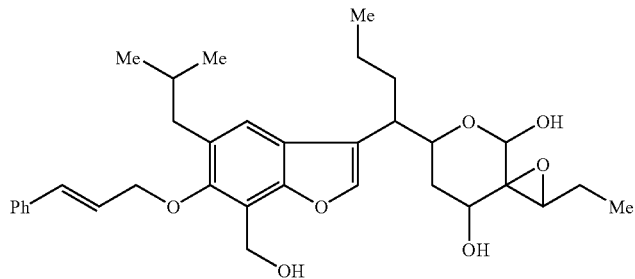<br>(−) enantiomer<br>C2' relative stereochemistry unknown |
| 805956 | 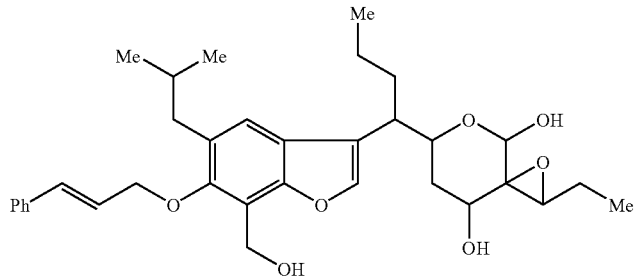<br>(+) enantiomer<br>C2' relative stereochemistry unknown |

-continued
| Ref. number | Compound |
|---|---|
| 806000 | 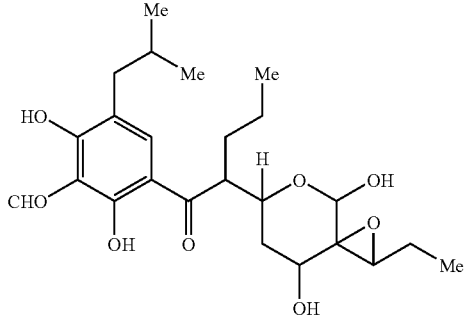<br>(−) enantiomer<br>C2' relative stereochemistry unknown |
| 806001 | 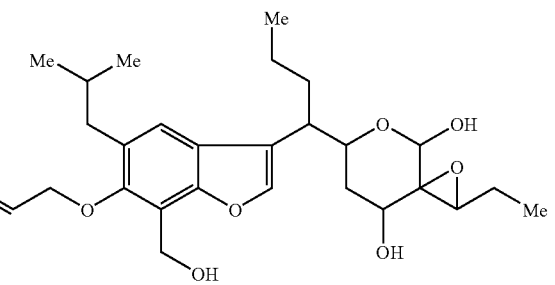<br>Racemic<br>C2' bottom, C3' Top |
| 806042 | 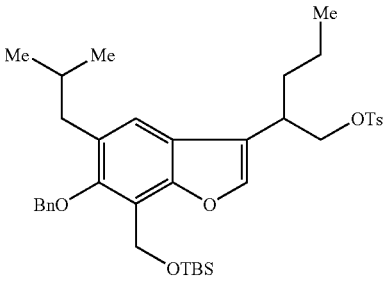 |
| 806043 | 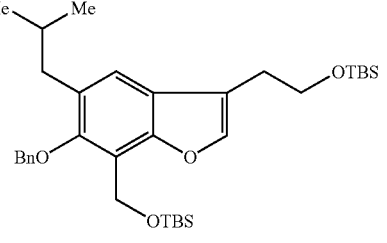 |
| 806710 | 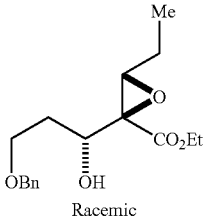<br>Racemic |

| Ref. number | Compound |
|---|---|
| 806711 | 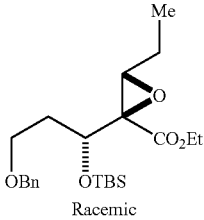 Racemic |
| 806712 | 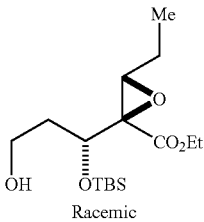 Racemic |
| 806768 | 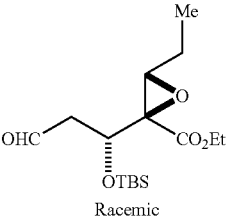 Racemic |
| 806769 | 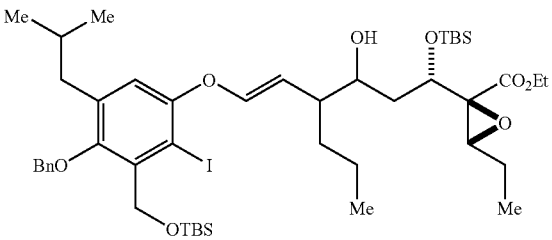 Racemic, Mixture of alcohols |
| 806770 | 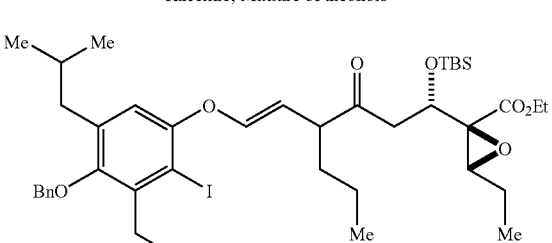 Racemic |

1) Experimental Procedures:

As described above, the present invention provides novel luminacin analogs having formula (I) as described above and in certain classes and subclasses herein. The synthesis of certain exemplary compounds is described in detail below. It will be appreciated that the methods as described herein can be applied to each of the compounds as disclosed herein and equivalents thereof. Additionally, certain regents and starting materials are well known to those skilled in the art. Although the following examples describe certain exemplary compounds, it will be appreciated that the use of alternate starting materials will readily yield other analogues encompassed by the invention.

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, or by proton nuclear magnetic resonance, of a suitably worked up sample of the reaction mixture.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (eg. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, then filtered. The crude products were then isolated by removal of solvent(s) by rotary evaporation under reduced pressure, at an appropriate temperature (generally less than 45° C.).

On occasions where triphenylphosphine oxide was a major byproduct of the reaction, the reaction mixture was added directly to a large volume of well-stirred hexane. The resultant precipitate of triphenylphosphine oxide was removed by filtration and the filtrate processed in the usual manner.

General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

Example 1

Preparation of Compound VD-1207D

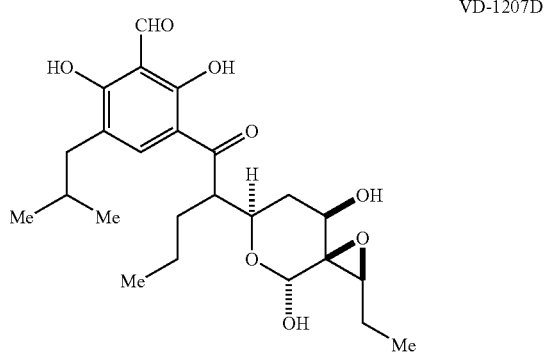

Preparation of Compound 3

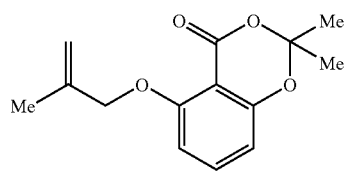

2,2-Dimethyl-5-Hydroxy-4-oxo-benzo-1,4-Dioxin (100 g, 0.515 mol) was dissolved in 500 mL of DMF. To this solution was added methallyl chloride (75 mL, 0.760 mol), NaI (10 g, 0.066 mol), and $K_2CO_3$ (100 g, 0.724 mol) and the solution was stirred with a mechanical stirrer for 7 hours. At this point, 1 L (10 vol) of $H_2O$ was added dropwise keeping the reaction temperature below 33° C. The reaction was then cooled to 5° C. and the product precipitated. The white solid was collected by filtration and then redissolved in IPA (300 mL, 3 vol) by heating to approx. 67° C. Reaction cooled to approx 49° C. and $H_2O$ (300 ml, 3 vol) was added to precipitate desired product (109.8 g, 85.8%).

Preparation of Compound 4

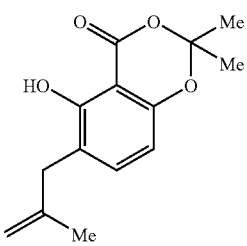

Compound 3 (10 g, 0.403 mol) was added to a 3-neck round bottom flask equipped with a $N_2$ outlet, JKEM temperature control, mechanical stirrer and heated to 210° C. The product was used with out purification in the next reaction.

Preparation of Compound 5

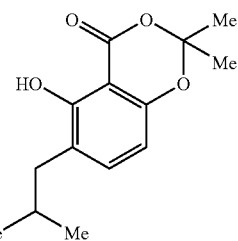

The unpurified product 4 was then dissolved into reagent grade alcohol. Pd/C 10% by wt was then added and placed tinder 1 atm of $H_2$. After reaction is complete, Pd/C is filtered off through a pad of celite. After rinsing the filter cake with reagent grade alcohol there was approximately 600 mL of the filtrate. To this was added approximately 150 mL of $H_2O$. At this point, the desired product precipitates from solution. The precipitate was collected and dried to obtain a white solid. (15 g, 74%, two steps).

Preparation of Compound 6

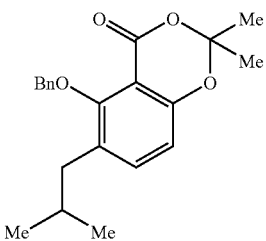

6

Compound 5 (11 g, 44 mmol) was dissolved in DMF (44 mL) at RT followed by the addition of $K_2CO_3$ (12 g, 88 mmol). To this stirred solution was added BnBr (11 g, 66 mmol) and stirred for 12 hours. The reaction mixture was then filtered through celite, washed with $CH_2Cl_2$, and the organics concentrated. The crude oil was then purified by passing through a plug of silica and eluting with 20:1 hexanes:EtOAc. (14.8 g, 99%).

Preparation of Compound 7

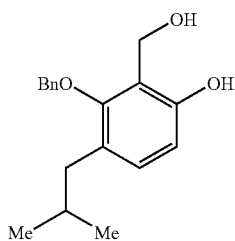

7

Compound 6 (3 g, 8.82 mmol) was dissolved in 30 mL of THF and cooled to 0° C. LAH (336 mg, 8.82 mmol) was then added portion wise. Reaction progress was monitored by TLC analysis and was complete after 1 hour. Reaction was quenched with 1N HCl followed by Rochell's salt and stirred for 1 hour. The aqueous layer was then washed with EtOAc (3×100 mL) and the combined organic layers dried over $Mg_2SO_4$. The crude material was then purified by flash column chromatography and eluted with 3:1 Hexanes:EtOAc to obtain a clear colorless oil which solidified upon standing (1.95 g, 77%).

Preparation of Compound 8

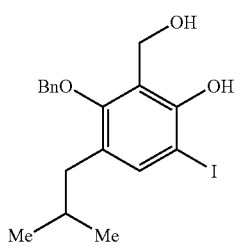

8

Compound 7 (4.54 g, 15.88 mmol) was dissolved in 80 mL of $CH_2Cl_2$ and cooled to 0° C. To this was added NIS (3.57 g, 15.88 mmol) and reaction allowed to warm to RT. Reaction was complete after 2 hours and quenched by addition of $Na_2HCO_3$ and the 1N $Na_2SO_3$. The aqueous layers were washed with $CH_2Cl_2$ (3×50 mL) and the combined organics dried over $MgSO_4$. The crude product was then purified by flash column chromatography and eluted with 5:1 hexanes: EtOAc. (3.78 g, 58%).

Preparation of 3-Benzyloxy-1-propanal (9)

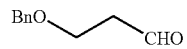

9

Oxallyl Chloride (102.6 mL, 205.14 mmol) was dissolved in 600 mL of $CH_2Cl_2$ and cooled to −78° C. DMSO (25.5 mL, 394.5 mmol) was then added through an addition funnel followed by 3-benzyloxy-1-propanol (25 mL, 157.8-mmol) dissolved in 200 mL of $CH_2Cl_2$, then $Et_3N$ (109.9 mL, 789 mmol). The reaction mixture was then allowed to warm to room temp and left to stir overnight. Reaction mixture was then diluted with approx. 600 mL of water and the organic layer separated. The aqueous layer was then washed with 2×300 mL of $CH_2Cl_2$. Organics were combined, dried over $MgSO_4$, and concentrated. The crude oil was purified by flash chromatography eluting with Hex/EtOAc (6/1).

Preparation of E and Z-(10)

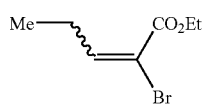

10

Sodium hydride 60% (39.25 g, 981 mmol) was dissolved in 750 ml of THF in a 3 necked round bottom flask, cooled to 0° C. and placed under a nitrogen atmosphere. Triethyl phosphonoacetate (200 g, 892 mmol) diluted in 500 ml of THF was added via cannula and the reaction mixture was stirred for 20 minutes. Bromine (156.83 g, 981 mmol) was added dropwise and the reaction mixture was stirred for 10 minutes. Sodium hydride 60% (39.25 g, 981 mmol) was added portionwise and the reaction mixture was stirred for 30 min at 0° C. After letting the reaction warm to room temperature, propanaldehyde (981 mmol) was dissolved in 200 ml of THF and added dropwise to the reaction mixture and stirred for 16 hrs at room temperature. Reaction was quenched with brine (700 ml) and the aqueous phase washed with ethyl acetate (3×500 ml). The combined organics were dried over magnesium sulfate, filtered and then concentrated. Purification by column chromatography (100:1 hexanes:ethyl acetate) afforded 289 g (97%) of a 50/50 E, Z mixture of 10 which could be partially separated.

Preparation of Compound 11

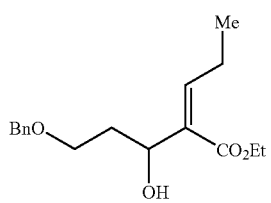

±11

Aldehyde 9 (39.36 g, 0.24 mol) was combined with vinyl bromide 10 (90.7 g, 0.47 mol) and placed under an atmosphere of nitrogen. The mixture was then dissolved in 2.3 L of DMF and secured in the fume hood. Ni/Cr (0.5% in Ni, 88 g, 0.72 mol) was then weighed into three batches approx. 29.3 g in the dry box. The catalyst was removed from the dry box and added to the rxn mixture in the fume hood in three batches (careful of exotherm). Rxn left to stir overnight. TLC analysis indicated that all aldehyde was consumed. At this point, the rxn was quenched with sodium serinate solution approx. 1 L and stirred in the presence of MTBE for one hour. Organics were separated and the aqueous layer washed with MTBE 3×400 mL. Organic layers were combine, dried over $Na_2SO_4$, and concentrated. The Crude green oil was purified by silica gel chromatography eluting with 6:1 Hexanes:Ethyl acetate to obtain 29.8 g of 11 (44% based on aldehyde) as a single olefin isomer.

Preparation of Compound 12

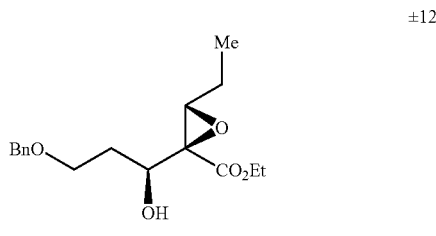

Alyllic alcohol 11 (19.76 g, 67.7 mmol) was dissolved in 340 mL of $CH_2Cl_2$ followed by the addition of 20 g of 4 Å MS. The reaction was then cooled down to −5° C. by submerging into a cryocool bath. At this time, $Ti(OiPr)_4$ (4.03 mL, 13.53 mmol) was then added (solution turned yellow) followed by the addition of t-butylhydroperoxide (5-6 M in nonane, 11.33 ml, 62.32 mmol) and left to stir overnight at −5° C. Reaction was still not complete after 12 hours and 10 g of 4 Å MS, 2 mL if $Ti(OiPr)_4$, and 10 mL of t-butylhydroperoxide were added. The reaction was complete after 1 additional hour. The reaction was quenched by the addition of Sat. sodium sulfite (400 ml). Celite was then added to the mixture, stirred for 10 min, and filtered through a pad of celite. The pad was washed thoroughly with 300 mL of $CH_2Cl_2$ and then the aqueous layers washed with $CH_2Cl_2$. The organics were then dried over $Na_2SO_4$ and concentrated to obtain a slightly yellow oil which was purified by silica gel (650 g) chromatography eluting with 2:1 MTBE:Hexanes to obtain 14.3 g (68%) of 12.

Preparation of Compound 13

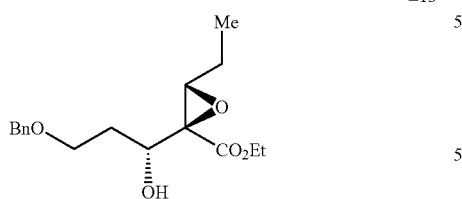

The epoxy alcohol 12 (4.64 g, 15 mmol) was dissolved in $CH_2Cl_2$ (100 ml) at room temperature under nitrogen. Triphenyl phosphine (4.34 g, 16.57 mmol) was added followed by p-nitrobenzoic acid (2.77 g, 16.57 mmol). DIAD (3.26 ml, 16.57 mmol) was added dropwise. After a couple of hours, the reaction was quenched with $H_2O$ and the aqueous layer washed with EtOAc. The organic layer was dried over $Na_2SO_4$ and concentrated to obtain a yellow oil. The crude material was purified by silica gel column, eluting with MTBE/hexanes (1:3). Fractions containing desired product were combined and concentrated to give a white solid with a 34% yield.

The p-nitrobenzoate (2.12 g, 4.64 mmol) was dissolved in EtOH (10 ml) and $K_2CO_3$ (1.92 g, 13.93 mmol) was added. The suspension was stirred at room temperature for 2 hours. EtOH was removed, $H_2O$ added and the aqueous layer washed with EtOAc. The organics were dried over $Na_2SO_4$ and concentrated to obtain a yellow oil. The crude material was purified by silica gel column, eluting with MTBE/hexan (1:3). Fractions containing desired product were combined to give a colorless oil with a 65% yield.

Preparation of Compound 14

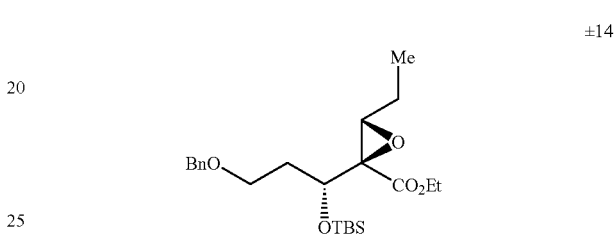

Compound 13 (6.05 g, 20.6 mmol) was dissolved in 100 ml of $CH_2Cl_2$ and then cooled to 0° C. $Et_3N$ (3.73 ml, 26.78 mmol) was then added followed by TBSOTf (5.2 ml, 22.66 mmol). The reaction was complete in 30 min. Quenched with MeOH (20 ml), concentrated, and then the crude oil was purified by silica gel chromatography eluting with 6:1 hexanes:EtOAc to obtain 7.31 g of 14 (87%). Alternatively, 13 (0.83 g, 2.82 mmol) was dissolved in DMF at RT, followed by the addition of TBSCI (0.62 g, 4.11 mmol) and imidizole (0.36 g, 5.29 mmol). Reaction mixture was stirred overnight. DMF was removed in vacuo and the oil redisolved in $H_2O$. The aqueous layer was then washed with EtOAc (3×20 ml) and dried over $Na_2SO_4$. The crude oil was purified by silica gel chromatography eluting with 6:1 hexanes:EtOAc to obtain 0.93 g of 14 (82%).

Preparation of Compound 15

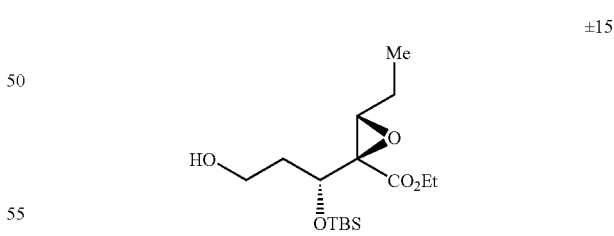

Compound 14 (911 mg, 2.16 mmol) was dissolved in 12 ml of THF at RT. $Pd(OH)_2/C$ 20% (45 mg, 5%/wt) was then added and reaction vessel placed under 1 atm of $H_2$ and stirred at RT for 4 hrs. At this point, another 5%/wt of $Pd(OH)_2/C$ was added and reaction was complete after an additional 2 hrs. The catalyst was removed by filtration through a pad of celite and rinsed with EtOAc. Obtained 717 mg (100%) of 14 as a crude oil and used directly in the next reaction. Note: deprotection with Pd/C was unsuccessful.

Preparation of Compound 16

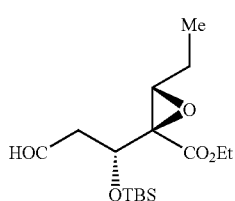

(COCl)₂ (1.73 ml, 3.46 mmol) was dissolved in 6 ml of CH₂Cl₂ and cooled to −78° C. followed by the addition of DMSO (460 ml, 6.48 mmol) dropwise. The crude oil 15 (717 mg, 2.16 mmol) in 4 ml of CH₂Cl₂ (rinse 2 ml) was then added dropwise followed by Et₃N. Reaction was stirred at −78° C. for 5 min and then warmed to RT and stirred for 30 min. Reaction was quenched with H₂O and the aqueous layer washed 3×30 ml with CH₂Cl₂. The combined organics were then dried with Na₂SO₄ and then concentrated. The crude oil was then purified by silica gel chromatography and eluted with 10:1, 6:1, 4:1, 3:1 hexanes:EtOAc to obtain 612 mg (86% for 2 steps).

Preparation of Compound 17

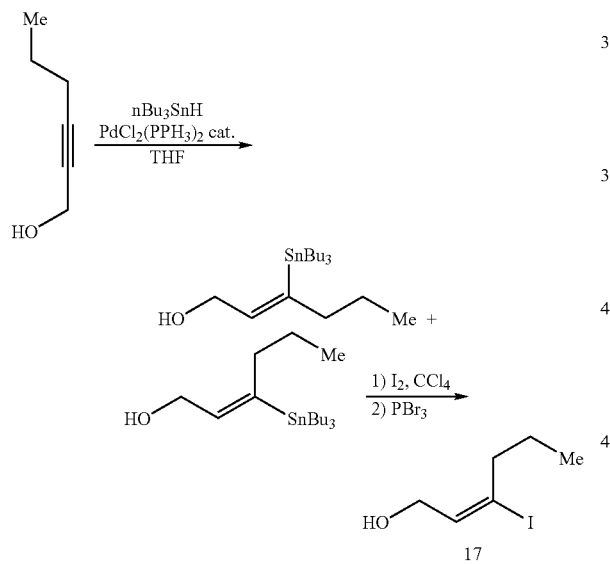

Procedure A: Commercially available 2-hexyne-1-ol (28.1 g, 286.32 mmol) was dissolved in 600 ml of THF in a 3 L flask. PdCl₂(Ph₃P)₂ (4.02 g, 5.73 mmol) was then added followed by the dropwise addition of nBu₃SnH via addition funnel. Reaction mixture was then stirred overnight and complete by TLC analysis. 500 ml of NaHCO₃ was then added to quench the reaction. THF was stripped down and the aqueous layer washed with 3×500 ml EtOAc. The organics were combined, dried over anhydrous MgSO₄ and concentrated. The crude oil was purified by silica gel chromatography eluting with 50:1, 20:1, 10:1, 3:1 hexanes:ethyl acetate to obtain 54.3 g (39%) of the undesired E-isomer and 16.6 g (15%) of the desired Z-isomer. The Z-isomer (16.5 g, 42.4 mmol) was then dissolved in 150 ml of CH₂Cl₂ and cooled to 0° C. I₂ was then dissolved in 300 ml of CH₂Cl₂ and added dropwise until a red color persisted. The CH₂Cl₂ was then removed in vacuo and the crude oil purified by silica gel chromatography eluting with 10:1, 8:1, 5:1, 3:1 hexanes:EtOAc. The compound was then washed with sodiumthiosulfate to remove any excess iodine. Concentration of the organics provided 8.5 g (95%) of the desired Z-vinyl iodide.

Preparation of Compound 18

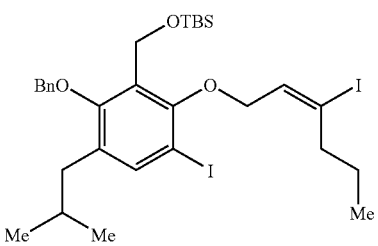

Compound 8 (3 g, 7.28 mmol) was dissolved in 40 mL of CH₃CN followed by the addition of 17 (2.5 g, 8.74 mmol) and K₂CO₃ (1.2 g, 8.74 mmol) and stirred at RT for 12 hours. Reaction complete by TLC and quenched with H₂O. The aqueous layers were washed with EtOAc (3×50 mL) and the combined organics dried over Mg₂SO₄. The organics were concentrated to obtain a yellow oil which was then dissolved in 50 mL of DMF. To this solution was added imidizole (1.12 g, 16.5 mmol), TBSCI (1.65 g, 11.0 mmol) and stirred at RT overnight. DMF was then removed on high vacuum, H₂O added, and aqueous layer washed with EtOAc (3×50 mL). Crude product was then purified by flash column chromatography and eluted with 8:1 hexanes:EtoAc. (78% two steps).

Preparation of Compound 19

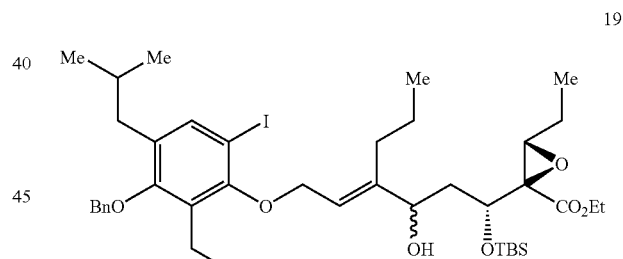

Aldehyde 16 (612 mg, 1.86 mmol) and vinyl iodide 18 (1.63 g, 2.23 mmol) were combined in a 25 ml round bottom flask with a stir bar. O₂ was removed by placing under a vacuum and purging with N₂ three times. The reaction vessel was then brought into the dry box where DMSO (10 ml) was added followed by the slow and portion wise addition of Ni/Cr (0.5% Ni, 912 mg, 7.42 mmol) with rapid stirring of the reaction mixture. The reaction vessel was then removed from the dry box, secured in the fume hood, and stirred for 4 hrs. Reaction mixture was then poured into 100 ml of Sat. NH₄Cl and stirred overnight with 50 ml of MTBE. The aqueous layer was then washed 3×50 ml of MTBE and the organics combined, washed with Brine 100 ml, and dried over Na₂SO₄. The crude oil was purified by silica gel chromatography and eluted with 10:1, 6:1, 3:1 to obtain 1.27 g of 19 (73%) as a mixture of alcohol diastereomers.

Preparation of Compound 20

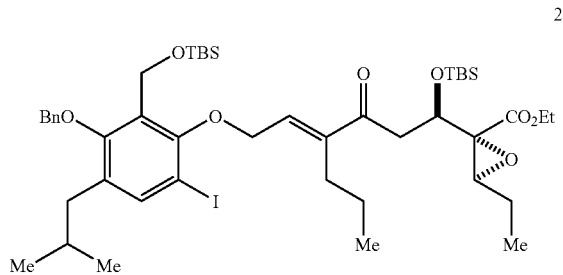

Allylic alcohol 19 (808 mg, 0.861 mmol) was dissolved in 5.7 mL of $CH_2Cl_2$ followed by the addition of 4 Å MS (1.2 g, oven dried). To this stirred solution was added NMO (110 mg, 0.947 mmol) followed by TPAP (30 mg, 0.086 mmol) and stirred at RT. The reaction was complete by TLC analysis in 1 hour. The molecular sieves were filtered away by passing through a pad of celite and washing the pad with Ethyl acetate. The organics were concentrated and passed through a plug of silica gel, eluting with 3:1 Hexanes:EtOAc. Obtained 690 mg (85% yield) of a clear colorless liquid.

Preparation of Compounds 21a and 21b

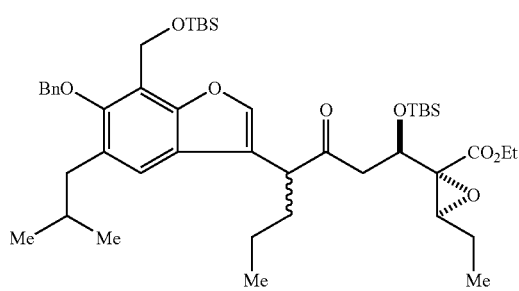

Ketone 20 (690 mg, 0.737 mmol) was dissolved in 7.5 mL of 1:1 $CH_3CN$:THF at RT. To this stirred solution was added $Et_3N$ (205 mL, 1.47 mmol) followed by Pd(dba)$_2$ chloroform adduct (38 mg, 0.37 mmol) and the reaction was heated to 70° C. The reaction progress was monitored by Mass spectrometry and completed after 5.5 hours. The reaction was cooled to RT, filtered through a pad of celite, concentrated, and purified by silica gel chromatography eluting with 7:1 Hexanes: MTBE. Obtained 536 mg (90%) as a clear colorless oil and a 1:1 mixture of propyl isomers. Separation of the propyl isomers was accomplished using a Dynamax Prep HPLC (77 mm column) eluting with 5% MTBE in hexanes, flow rate of 60 mL/min., monitoring at 254λ. Higher $R_f$ spot was assigned as 21a, lower $R_f$ spot was assigned as 21b. 21a can be equilibrated to 21b by the following procedure: 21a (3.8 g, 4.7 mmol) was dissolved in toluene (10 mL) and 1,8-diazabicyclo[5.4.0]undec-7-ene (143 mg, 0.97 mmol) was added. Stir at RT for 5 hours and quenched with $H_2O$ (1 mL). The mixture was extracted with EtOAc and the organic layer was dried over $MgSO_4$, filtered and concentrated to give a clear oil which was a 1:1 mixture of 21a and 21b. This mixture was separated and the pure 21b was obtained (1.7 g) in 45% yield.

Preparation of Compounds 22a and 22b

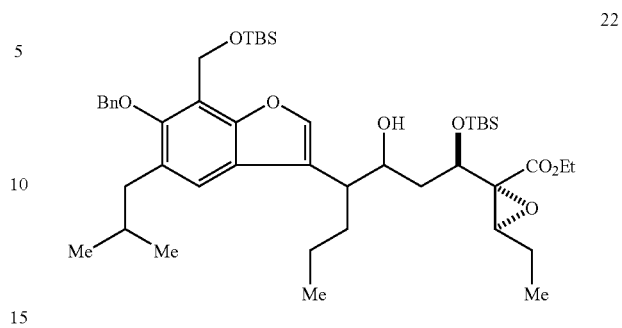

Ketone 21a higher Rf (64 2 mg, 0.795 mmol) was dissolved in 10 mL of MeOH and cooled to 0° C. To this stirred solution was added $NaBH_4$ (30 mg, 0.795 mmol). The reaction was monitored by TLC analysis and complete after 1.5 hours. The reaction mixture was then diluted with water and $CH_2Cl_2$ and stirred for 1 hour. Aqueous layer was then washed with $CH_2Cl_2$, EtOAc, and MTBE. The organics were then combined, dried over $Na_2SO_4$ and concentrated. The C3' isomers were separable by Preparative HPLC. Conditions: Dynamax Prep HPLC, 77 mm column, 10% MTBE in hexanes, flow rate of 120 mL/min, 254 λ, 175 mg/2 mL injection. Obtained 314 mg of the higher $R_f$ diastereomer (22a) and 256 mg of the lower $R_f$ diastereomer (22b) (Ratio 1.2:1, 88% combined yield).

Preparation of Compounds 22c and 22d 22c and 22d: Ketone 22b lower Rf (500 mg, 0.623 mmol) was dissolved in 5 mL of MeOH and cooled to 0° C. To this stirred solution was added $NaBH_4$ (23 mg, 0.623 mmol) and stirred at 0° C. for 1 hr. Reaction was quenched with water, the aqueous layers washed with EtOAc, and the organics dried over $Na_2SO_4$. The crude oil (ratio 2.1:1 mixture of C3' diastereomers) was purified by silica gel chromatography eluting with 8:1 Hexanes:MTBE to obtain the higher $R_f$ diastereomer 22c (284 mg, 57%) followed by 1:1 hexanes:MTBE to remove the lower $R_f$ diastereomer 22d (134 mg, 27%) for an overall yield of 84%.

Preparation of compound 23d

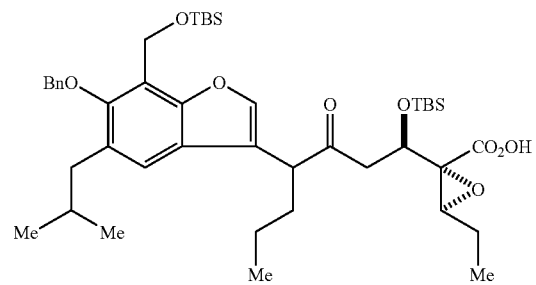

Ester 22d (134 mg, 0.166 mmol) was dissolved into 13 mL of THF followed by the addition of 3.3 mL of 2M LiOH. The reaction vessel was then equipped with a reflux condenser and heated to 50° C. The reaction was complete by TLC after 3 hours and allowed to cool to RT. The solution was neutralized with 1N HCl and the aqueous layers washed with EtOAc (3×10 mL). The organic layers were dried over $Na_2SO_4$ and concentrated to obtain 126 mg (97%) of a clear oil. The material was then used in the next reaction without any purification. (CJ-619-106). Note: The acid 23 is not stable and should not be stored. Upon storing compound in the freezer over the weekend one TBS group fell off.

Preparation of Compound 24d

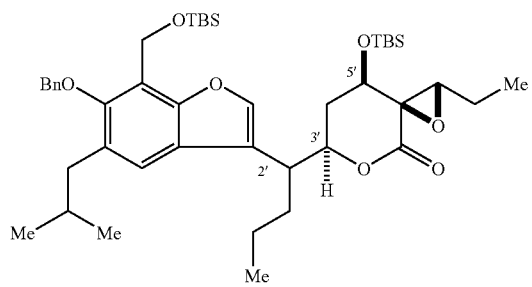

24d

Acid 23d (112 mg, 0.144 mmol) was dissolved in 15 mL of toluene followed by the addition of 2,4,6-tricholobenzoyl-chloride (25 µL, 0.158 mmol) and Et₃N (60 µL, 0.432 mmol). The reaction was stirred at RT for 20 min. before the addition of DMAP (19 mg, 0.158 mmol) which produces a cloudy white suspension. The reaction was complete by TLC analysis after 30 min and quenched with H₂O. The aqueous layers were then washed with EtOAc, dried over Na₂SO₄ and concentrated. The crude oil was purified by passing through a plug of silica eluting with 6:1 hexanes:EtOAc to obtain 109 mg (99%) of a colorless oil.

Preparation of Compound 25d

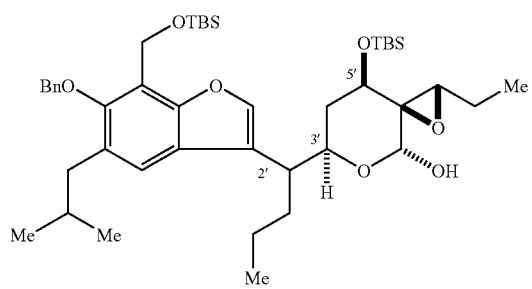

25d

Lactone 24d (49 mg, 0.064 mmol) was dissolved in 1 mL of toluene and cooled to −78° C. To this stirred solution was added Dibal (1M in CH₂Cl₂, 128 mL, 0.128 mmol). The reaction progress was monitored by mass spec. After 15 min, reaction was not complete. At this time 0.5 equiv. of Dibal was added. After 5 additional minutes, the reaction was complete. Quenched with Rochell's salt, extracted with EtOAc, and dried over Na₂SO₄ to obtain 50 mg of a colorless oil which was used without purification is the next reaction.

Preparation of Compound 26d

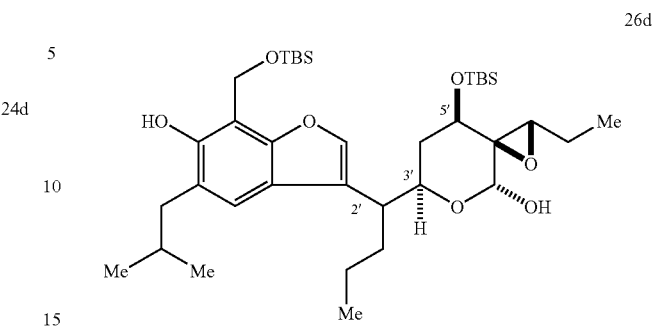

26d

Lactol 25d (50 mg, 0.64 mmol) was dissolved in 3 mL of EtOH followed by the addition W-2 Raney Ni (spatula tip, weight unknown comes in a solution in H₂O) at RT. Reaction progress was monitored by mass spec and is complete after 1 hour. The reaction was then filtered through celite and washed with CH₂Cl₂ and H₂O (careful not to let Raney Ni go dry). The aqueous layer is then washed with CH₂Cl₂, the organics dried over Na₂SO₄, and concentrated to obtain 33 mg (76%) of a colorless oil.

Preparation of Compound 27d

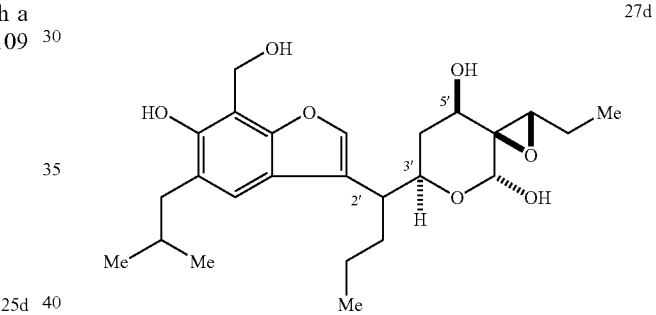

27d

Phenol 26d (32 mg, 0.048 mmol) was dissolved in 1 mL of THF and cooled to 0° C. TBAF (1M in THF, 122 µL, 0.122 mmol) was then added and after 45 min only the monodeprotected mass was detected by mass spec. Reaction was allowed to warm to RT and complete after 4.5 hours. Quenched with NH₄Cl, aqueous layers washed with EtOAc, and the combined organics dried over Na₂SO₄. The crude oil was used without further purification in the next reaction.

Preparation of Compound 28d

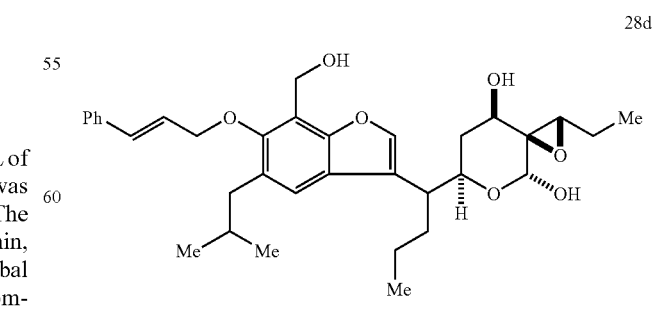

28d

Triol 27d (0.048 mmol) was dissolved in 5 mL of CH₃CN. To this solution was added solid K₂CO₃ (30 mg, 0.22 mmol)

and cinammyl bromide (11 mg, 0.058 mmol) and stirred at RT for 2 days. Reaction is monitored by TLC and mass spec. Quenched with H$_2$O, aqueous layers washed with EtOAc, and the combined organic layers dried over Na$_2$SO$_4$. The crude oil was purified by passing through a pipette column eluting with 2:1 MTBE:Hexanes to obtain 17 mg (63% for the two steps 26d→28d).

Preparation of Compound 29d

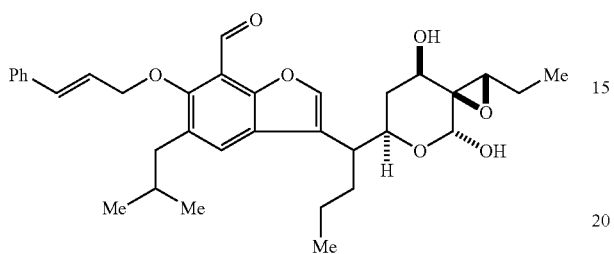

Lactol 28d (7 mg, 0.12 mmol) was dissolved in 3 mL of CH$_2$Cl$_2$ followed by the addition of MnO$_2$ (77 mg) at RT. Reaction progress monitored by TLC and after 1.5 hours, 8 mg more of MnO$_2$ was added. After 30 additional minutes, the reaction was complete. The reaction was then filtered through a plug of celite, washed with CH$_2$Cl$_2$, and concentrated. The crude material was used without purification in the next reaction.

Preparation of Compound 30d

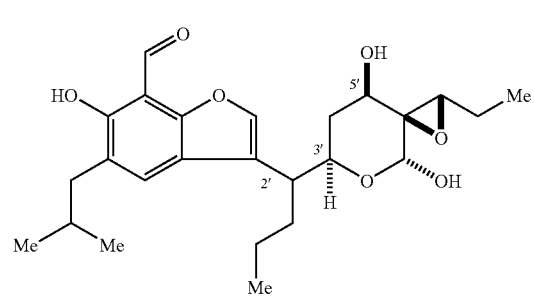

Aldehyde 29d (0.12 mmol) was dissolved in 2 mL of EtOH:H$_2$O (5:1) followed by Et$_3$N (75 μL, 0.54 mmol), PPh$_3$ (4 mg, 0.15 mmol), Pd(OAc)$_2$ (3 mg, 0.013 mmol), and formic acid (15 μL). The reaction was monitored by TLC and complete in 20 min. The reaction was neutralized with NaHCO$_3$, the aqueous layers washed with EtOAc, and then concentrated. The crude material was purified by Prep TLC (plates pre-eluted with MTBE) eluting with 2:1 MTBE:Hexanes. Obtained 0.97 mg of a yellow solid after lyophilization.

Preparation of VD-1207D

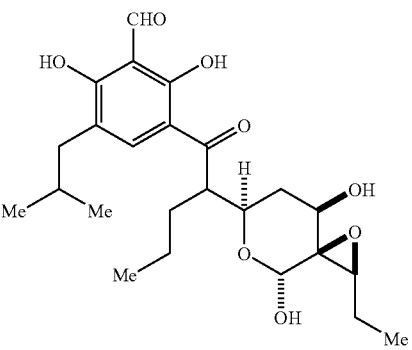

Benzofuran 30d (0.012 mmol) was dissolved in 2 mL of CH$_2$CL, and cooled to −78° C. O$_3$ is then bubbled in the reaction mixture for 20 seconds. By mass spec and TLC analysis, there was no starting material and the mass spec showed M-H for VD-1207D. At this time, 0.2 mL of Me$_2$S is added at −78° C. and then allowed to warm slowly to RT and stirred for 30 minutes. The reaction was then concentrated. Purification was accomplished by Prep TLC (plate pre-eluted with acetone) eluting with 7:3 Hexanes:Acetone or HPLC (ODS column, CH$_3$CN 50%, KH$_2$PO$_4$ buffer (pH=3.5) 50%, 1 mL/min.).

Note: Chiral HPLC Resolution 23d and 25d can be resolved by Chiral HPLC allowing access to each enantiomer of VD-1207D and subsequent analogs through the procedures described above. Conditions for Resolving 23d:

Chiral Technologies AD Chiralpak column (0.46 cm×25 cm).
Sample concentration: 17.55 mg/mL in 10:1 Hexanes:IPA
Flow rate: 1 mL/min.
Wavelength: 254
Injection volume: 10 μL
Retention time first peak: 5.47 min.
Retention time second peak: 9.22 min.
Note: 30 μL injection can also be separated (0.526 mg/injection).
Conditions for Resolving 25d:
Chiral Technologies AD Chiralpak column (2.0 cm×25 cm).
Sample concentration: 18.0 mg/mL in 15% IPA in hexanes
Flow rate: 6 mL/min.
Wavelength: 254
Injection volume: 500 μL
Retention time first peak: 36.42 min. (optical rotation=− 36.9° (0042, CHCl$_3$)
Retention time second peak: 32.6 min. (optical rotation=+ 35.7° (0.0041, CHCT$_3$)
Note: 2 injections produced 8 mg of each enantiomer.

Example 2

Biological Assays $^3$H-Thymidine Incorporation Assay for an Inhibitory Effect on the Proliferation of Human Umbilical Vein Endothelial Cells (HUVEC)

HUVEC (Cascade Biologies, Inc.) were seeded at a density of 5,000 cells per well in 96-well plates with M-200 complete growth medium (Cascade Biologies, Inc.) and incubated at 37° C. for three days. Cells were then serum-depleted by removing the growth medium and replacing it with M-200+ 0.5% fetal bovine serum followed by an overnight incubation at 37° C. Basic fibroblast growth factor (bFGF, Biosource International, Inc.) and compounds were incubated with the cells for 22 h followed by the addition of 1 µCi of 3H-thymidine (NEN) to each well. After 2 hours, the cells were harvested on a GF/B filter (Unifiler™-96, GF/BTM, Packard) using a 96-well cell harvester (Packard), and the filter was then washed with water and ethanol. Scintillation liquid (50 µL) was added to each well and counted in TopCount Microplate Counter NXT™(Packard).

Cytotoxicity Assay using HUVEC

HUVEC were seeded at a density of 5,000 cells per well in 96-well plates with M-200 complete growth medium and incubated at 37° C. for three days. Cells were then washed twice with M-200 medium and replaced with M-200+0.5% fetal bovine serum followed by an overnight incubation at 37° C. bFGF and compounds were incubated with the cells for 24 h. Cytotoxicity was evaluated with measuring ATP contents as a marker for cell viability using ATP-Lite™-M Luminescent ATP Detection Assay Kit (Packard). ATP-Lite™-M Luminescent ATP Detection Assay was performed by the manufacturer's protocol, briefly, cell lysis solution was mixed with the same volume of substrate solution followed by 1 h incubation at room temperature, then the luminescence was measured with TopCount Microplate Counter NXT™ (Packard).

The invention claimed is:

1. A compound having the structure of Formula I

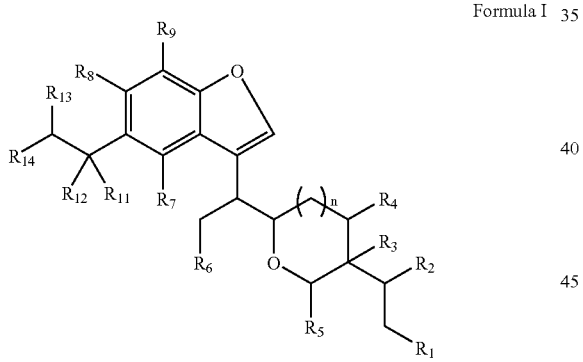

Formula I wherein n is 0, 1 or 2;
$R_1$ is hydrogen or an aliphatic, heteroaliphatic, aryl or heteroaryl moiety;
$R_2$ and $R_3$ are each independently hydrogen, or, when taken together, may be —O— or —(CH$_2$)$_q$—, wherein q is 1, 2 or 3;
$R_4$ is hydrogen, hydroxyl, protected hydroxyl or OR$^i$, or an aliphatic or heteroaliphatic moiety, wherein R$^i$ is an aliphatic or heteroaliphatic moiety;
$R_5$ is hydrogen, hydroxyl, protected hydroxyl or OR$^{ii}$, or an aliphatic or heteroaliphatic moiety, wherein R$^{ii}$ is an aliphatic or heteroaliphatic moiety, or wherein $R_1$ and $R_5$, when taken together, may form a cycloaliphatic or heterocycloaliphatic moiety comprising 6 to 12 atoms;
$R_6$ is hydrogen, or an aliphatic, heteroaliphatic, aryl or heteroaryl moiety;

$R_7$ is hydrogen, hydroxyl, protected hydroxyl, OR$^{iii}$, or an aliphatic or heteroaliphatic moiety, wherein R$^{iii}$ is an aliphatic or heteroaliphatic moiety;
$R_8$ is hydrogen, hydroxyl, protected hydroxyl or OR$^{iv}$, wherein R$^{iv}$ is an aliphatic or heteroaliphatic moiety;
$R_9$ is hydrogen, —CF$_3$, —CHO, imine, hydrazone, oxime, carboxylic acid, carboxylic ester, acyl halide, ketone, amide, acetal, anhydride, dihalide, epoxide, nitrile or an aliphatic or heteroaliphatic moiety;
$R_{11}$ and $R_{12}$ are each independently hydrogen, hydroxyl or OR$^v$, or an aliphatic or heteroaliphatic moiety, or, when taken together, may be —(C═O), wherein R$^v$ is an aliphatic or heteroaliphatic moiety; and
$R_{13}$ and $R_{14}$ are each independently hydrogen, or an aliphatic, heteroaliphatic, aryl or heteroaryl moiety;
wherein each of the aliphatic and heteroaliphatic moieties may independently be substituted or unsubstituted, cyclic or acyclic, linear or branched, and wherein each of the aryl and heteroaryl moieties may be substituted or unsubstituted;
with the proviso that when $R_4$, $R_5$, $R_8$ and $R_{10}$ are each hydroxyl, $R_{13}$ and $R_{14}$ are each methyl, $R_2$ and $R_3$, taken together, form an epoxide, and n is 1, the following groups do not occur simultaneously as defined:

$R_1$ is methyl, $R_9$ is hydrogen, ($R_{11}$, $R_{12}$) is (═O) and $R_6$ is ethyl or isopropyl;
$R_1$ is methyl, $R_9$ is CHO, ($R_{11}$, $R_{12}$) is (OMe, H) and $R_6$ is ethyl, propyl or isopropyl;
$R_1$ is methyl, $R_9$ is CHO, $R_{11}$ and $R_{12}$ are hydrogen and $R_6$ is ethyl, propyl or isopropyl;
$R_1$ is methyl, $R_9$ is COCH$_3$, $R_{11}$ and $R_{12}$ are hydrogen and $R_6$ is ethyl; and
$R_1$ is ethyl, $R_9$ is CHO, $R_{11}$ and $R_{12}$ are hydrogen and $R_6$ is ethyl.

2. The compound of claim 1, wherein n is 1 and the compound of Formula I has the structure:

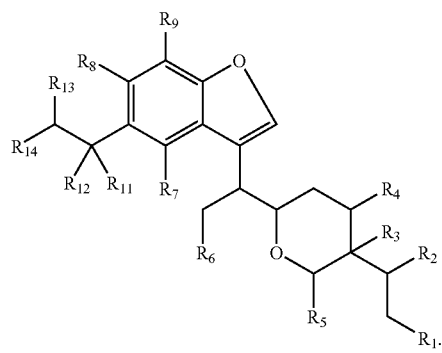

3. The compound of claim 1, wherein $R_{14}$ is aryl and the compound has the structure:

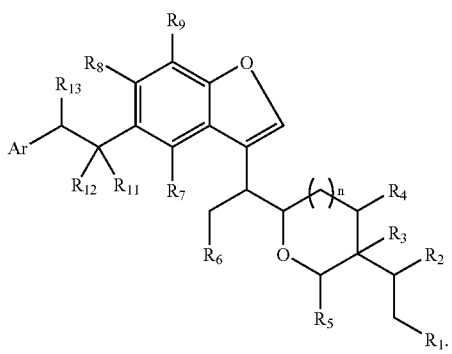

4. The compound of claim 1, wherein R₂ and R₃, taken together, form an epoxide and the compound has the structure:

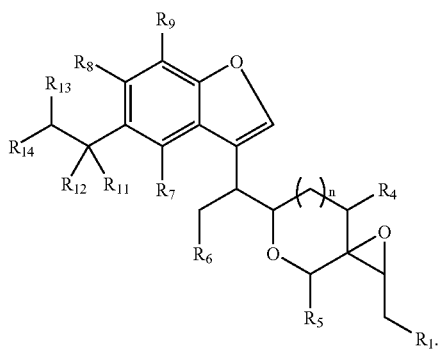

5. The compound of claim 1, wherein R₄ is hydroxyl and the compound has the structure:

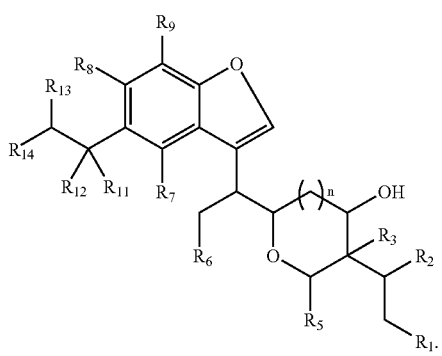

6. The compound of claim 1, wherein R₂ and R₃, taken together, form an epoxide, R₄ is hydroxyl, R₁₄ is aryl, n is 1 and the compound has the structure:

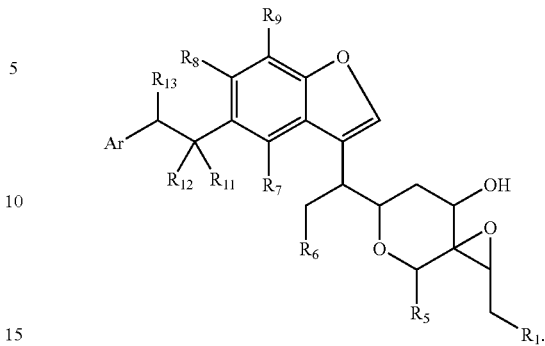

7. The compound of any one of claims 1, 2, 3, 4, 5 or 6, wherein R₁ is hydrogen or lower alkyl, and wherein the alkyl substituent may be substituted or unsubstituted, linear or branched or cyclic or acyclic.

8. The compound of any one of claims 1, 2, 3 or 5, wherein R₂ and R₃, taken together, form a cyclopropyl moiety.

9. The compound of any one of claims 1, 2, 3 or 5, wherein R₂ and R₃, taken together, form an epoxide.

10. The compound of any one of claims 1, 2, 3 or 4, wherein R₄ is hydroxyl.

11. The compound of any one of claims 1, 2, 3, 4, 5 or 6, wherein R₅ is hydroxyl or lower alkoxyl, and wherein the alkoxyl substituent may be substituted or unsubstituted, linear or branched or cyclic or acyclic.

12. The compound of any one of claims 1, 2, 3, 4, 5 or 6, wherein R₆ is lower alkyl, and wherein the alkyl substituent may be substituted or unsubstituted, linear or branched or cyclic or acyclic.

13. The compound of any one of claims 1, 2, 3, 4, 5 or 6, wherein R₇ is hydrogen, hydroxyl, lower alkyl or lower alkoxyl, and wherein the alkyl and alkoxyl substituents may be substituted or unsubstituted, linear or branched or cyclic or acyclic.

14. The compound of any one of claims 1, 2, 3, 4, 5 or 6, wherein R₈ is hydrogen, hydroxyl or protected hydroxyl.

15. The compound of any one of claims 1, 2, 3, 4, 5 or 6, wherein R₉ is —CHO or —CH₂OR$^{vi}$, wherein R$^{iv}$ is hydrogen, protecting group or an aliphatic moiety, and wherein the aliphatic moiety may be substituted or unsubstituted, linear or branched or cyclic or acyclic.

16. The compound of any one of claims 1, 2, 3, 4, 5 or 6, wherein R₁₁ and R₁₂ are independently hydrogen or lower alkoxyl, and wherein the alkoxyl substituent may be substituted or unsubstituted, branched or unbranched or cyclic or acyclic.

17. The compound of any one of claims 1, 2, 4, or 5, wherein $R_{13}$ and $R_{14}$ are independently hydrogen, lower alkyl or aryl, wherein the alkyl substituent may be substituted or unsubstituted, branched or unbranched or cyclic or acyclic, and wherein the aryl substituent may be substituted or unsubstituted.

18. The compound of claim 3 or 6, wherein $R_{13}$ is lower alkyl, and wherein the alkyl substituent may he substituted or unsubstituted, linear or branched or cyclic or acyclic.

19. The compound of claim 6, wherein $R_1$ is hydrogen or lower alkyl, $R_5$ is hydroxyl or lower alkoxyl, $R_6$ is lower alkyl, $R_7$ is hydrogen, hydroxyl, lower alkyl or lower alkoxyl, $R_8$ is hydrogen, hydroxyl or protected hydroxyl, $R_9$ is —CHO or —CH$_2$OR$^{vi}$, $R_{11}$ and $R_{12}$ are independently hydrogen or lower alkoxyl, and $R_{13}$ is lower alkyl; wherein $R^{vi}$ is hydrogen, protecting group or an aliphatic or heteroaliphatic moiety;

wherein each of the alkyl, alkoxyl, aliphatic and heteroaliphatic moieties may be independently substituted or unsubstituted, linear or branched, or cyclic or acyclic.

20. The compound of claim 1 having the following structure:

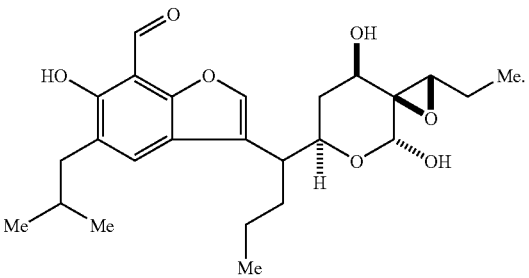

21. The compound of claim 6, wherein $R_{13}$ is hydrogen, lower alkyl or aryl, wherein the alkyl substituent may be substituted or unsubstituted, branched or unbranched or cyclic or acyclic, and wherein the aryl substituent may be substituted or unsubstituted.

* * * * *

UNITED STATES PATENT AND TRADEMARK OFFICE
CERTIFICATE OF CORRECTION

| | | |
|---|---|---|
| PATENT NO. | : 7,642,284 B2 | Page 1 of 1 |
| APPLICATION NO. | : 12/100194 | |
| DATED | : January 5, 2010 | |
| INVENTOR(S) | : Fang et al. | |

It is certified that error appears in the above-identified patent and that said Letters Patent is hereby corrected as shown below:

In the Claims:

Column 81, Claim 18, Line 9: Please correct "may he substituted"
to read -- may be substituted --

Signed and Sealed this

Twentieth Day of April, 2010

David J. Kappos
*Director of the United States Patent and Trademark Office*